US010682219B2

(12) United States Patent
Foote et al.

(10) Patent No.: US 10,682,219 B2
(45) Date of Patent: Jun. 16, 2020

(54) FIXATION OF INTRALUMINAL DEVICE

(71) Applicant: BFKW, LLC, Grand Rapids, MI (US)

(72) Inventors: James A. Foote, Ada, MI (US); Frederick J. Walburn, Grand Rapids, MI (US); Randal S. Baker, Grand Rapids, MI (US)

(73) Assignee: BFKW, LLC, Ada, MI (US)

( * ) Notice: Subject to any disclaimer, the term of this patent is extended or adjusted under 35 U.S.C. 154(b) by 315 days.

(21) Appl. No.: 15/534,891

(22) PCT Filed: Dec. 22, 2015

(86) PCT No.: PCT/US2015/067407
§ 371 (c)(1),
(2) Date: Jun. 9, 2017

(87) PCT Pub. No.: WO2016/109346
PCT Pub. Date: Jul. 7, 2016

(65) Prior Publication Data
US 2017/0360550 A1 Dec. 21, 2017

Related U.S. Application Data

(60) Provisional application No. 62/234,335, filed on Sep. 29, 2015, provisional application No. 62/151,150, (Continued)

(51) Int. Cl.
*A61F 2/04* (2013.01)
*A61B 17/064* (2006.01)
*A61F 5/00* (2006.01)

(52) U.S. Cl.
CPC .............. *A61F 2/04* (2013.01); *A61B 17/064* (2013.01); *A61F 5/0036* (2013.01);
(Continued)

(58) Field of Classification Search
CPC .............. A61F 2/848; A61F 2220/0016; A61F 2220/0008; A61F 2002/045; A61F 2002/044
See application file for complete search history.

(56) References Cited

U.S. PATENT DOCUMENTS

| 4,403,604 A | 9/1983 | Wilkinson et al. |
| 4,607,618 A | 8/1986 | Angelchik |

(Continued)

FOREIGN PATENT DOCUMENTS

| EP | 0760696 B1 | 8/2001 |
| EP | 1808888 A2 | 7/2007 |

(Continued)

OTHER PUBLICATIONS

International Search Report of the International Searching Authority from corresponding Patent Cooperation Treaty (PCT) Patent Application No. PCT/US12/38480, dated Jul. 30, 2012.

(Continued)

*Primary Examiner* — Diane D Yabut
(74) *Attorney, Agent, or Firm* — Gardner Linn

(57) ABSTRACT

An intraluminal device and method of fixation of an intraluminal device to resist distal migration in a mammalian lumen or hollow organ that is subject to peristalsis, according to an aspect of the invention, includes spaced apart wall portions connected with a connector. The wall portions are configured to the size and shape of a portion of the lumen or hollow organ and the connector is configured to be positioned against a wall of the lumen or hollow organ. The intraluminal device is positioned in a mammalian lumen or hollow organ that is subject to peristalsis. The device is fixed in the lumen or hollow organ against distal migration, wherein tissue lining the lumen or hollow organ bridges over the connector. The device is explanted after tissue bridges over the connector including separating the connector from (Continued)

one or both of the wall portions and withdrawing the connector axially from the tissue bridging over the connector.

38 Claims, 20 Drawing Sheets

Related U.S. Application Data filed on Apr. 22, 2015, provisional application No. 62/115,689, filed on Feb. 13, 2015, provisional application No. 62/097,295, filed on Dec. 29, 2014.

(52) U.S. Cl.
CPC .......... *A61F 5/0069* (2013.01); *A61F 5/0089* (2013.01); *A61B 2017/0641* (2013.01); *A61F 2002/044* (2013.01); *A61F 2002/045* (2013.01); *A61F 2220/0016* (2013.01); *A61F 2220/0033* (2013.01); *A61F 2230/0093* (2013.01); *A61F 2250/006* (2013.01)

(56) References Cited

U.S. PATENT DOCUMENTS

| | | | |
|---|---|---|---|
| 5,234,454 A | 8/1993 | Bangs | |
| 5,306,300 A | 4/1994 | Berry | |
| 5,366,504 A | 11/1994 | Andersen et al. | |
| 5,507,755 A | 4/1996 | Gresl et al. | |
| 5,662,713 A | 9/1997 | Andersen et al. | |
| 5,741,279 A | 4/1998 | Gordon et al. | |
| 5,820,584 A | 10/1998 | Crabb | |
| 6,146,416 A | 11/2000 | Andersen et al. | |
| 6,264,700 B1 | 7/2001 | Kilcoyne et al. | |
| 6,280,415 B1 | 8/2001 | Johnson | |
| 6,312,437 B1 | 11/2001 | Kortenbach | |
| 6,355,070 B1 | 3/2002 | Andersen et al. | |
| 6,398,802 B1 | 6/2002 | Yee | |
| 6,432,040 B1 | 8/2002 | Meah | |
| 6,447,533 B1 | 9/2002 | Adams | |
| 6,468,298 B1 | 10/2002 | Pelton | |
| 6,544,291 B2 | 4/2003 | Taylor | |
| 6,558,400 B2 | 5/2003 | Deem et al. | |
| 6,572,627 B2 | 6/2003 | Gabbay | |
| 6,656,194 B1 | 12/2003 | Gannoe et al. | |
| 6,675,809 B2 | 1/2004 | Stack et al. | |
| 6,736,828 B1 | 5/2004 | Adams et al. | |
| 6,740,121 B2 | 5/2004 | Geitz | |
| 6,746,460 B2 | 6/2004 | Gannoe et al. | |
| 6,755,869 B2 | 6/2004 | Geitz | |
| 6,773,440 B2 | 8/2004 | Gannoe et al. | |
| 6,800,081 B2 | 10/2004 | Parodi | |
| 6,802,868 B2 | 10/2004 | Silverman et al. | |
| 6,845,776 B2 | 1/2005 | Stack et al. | |
| 6,916,332 B2 | 7/2005 | Adams | |
| 6,960,233 B1 | 11/2005 | Berg et al. | |
| 6,981,978 B2 | 1/2006 | Gannoe | |
| 6,994,095 B2 | 2/2006 | Burnett | |
| 6,994,715 B2 | 2/2006 | Gannoe et al. | |
| 7,025,791 B2 | 4/2006 | Levine et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,044,979 B2 | 5/2006 | Silverman et al. | |
| 7,066,945 B2 | 6/2006 | Hashiba et al. | |
| 7,083,629 B2 | 8/2006 | Weller et al. | |
| 7,083,630 B2 | 8/2006 | DeVries et al. | |
| 7,087,088 B2 | 8/2006 | Berg et al. | |
| 7,097,650 B2 | 8/2006 | Weller et al. | |
| 7,097,665 B2 | 8/2006 | Stack et al. | |
| 7,111,627 B2 | 9/2006 | Stack et al. | |
| 7,146,984 B2 | 12/2006 | Stack et al. | |
| 7,152,607 B2 | 12/2006 | Stack et al. | |
| 7,211,114 B2 | 5/2007 | Bessler et al. | |
| 7,220,284 B2 | 5/2007 | Kagan et al. | |
| 7,232,461 B2 | 6/2007 | Ramer | |
| 7,347,875 B2 | 3/2008 | Levine et al. | |
| 7,431,725 B2 | 10/2008 | Stack et al. | |
| 7,445,010 B2 | 11/2008 | Kugler et al. | |
| 7,449,024 B2 | 11/2008 | Stafford | |
| 7,682,330 B2 | 3/2010 | Meade et al. | |
| 7,704,264 B2 | 4/2010 | Ewers et al. | |
| 7,708,752 B2 | 5/2010 | Durgin | |
| 7,753,870 B2 | 7/2010 | Demarais et al. | |
| 7,771,382 B2 | 8/2010 | Levine et al. | |
| 7,815,589 B2 | 10/2010 | Meade et al. | |
| 7,815,591 B2 | 10/2010 | Levine et al. | |
| 7,846,174 B2 | 12/2010 | Baker et al. | |
| 7,922,650 B2 | 4/2011 | McWeeney et al. | |
| 7,976,488 B2 | 7/2011 | Levine et al. | |
| 7,981,163 B2 | 7/2011 | Meade et al. | |
| 8,029,455 B2 | 10/2011 | Stack et al. | |
| 8,043,355 B2 | 10/2011 | Shin et al. | |
| 8,100,931 B2 | 1/2012 | Baker et al. | |
| 8,137,301 B2 | 3/2012 | Levine et al. | |
| 8,162,871 B2 | 4/2012 | Levine et al. | |
| 8,282,598 B2 | 10/2012 | Belhe et al. | |
| 8,372,087 B2 | 2/2013 | Baker et al. | |
| 8,447,403 B2 | 5/2013 | Sharma et al. | |
| 8,506,477 B2 | 8/2013 | Waller et al. | |
| 8,529,431 B2 | 9/2013 | Baker et al. | |
| 8,556,956 B2 | 10/2013 | Cully et al. | |
| 8,672,831 B2 | 3/2014 | Baker et al. | |
| 8,721,528 B2 | 5/2014 | Ho et al. | |
| 8,778,011 B2 | 7/2014 | Ryan | |
| 8,784,436 B2 | 7/2014 | Ho et al. | |
| 8,801,599 B2 | 8/2014 | Baker et al. | |
| 8,894,670 B2 | 11/2014 | Baker et al. | |
| 9,055,998 B2 | 6/2015 | Baker | |
| 9,107,742 B2 | 8/2015 | Cully et al. | |
| 9,198,789 B2 | 12/2015 | Baker et al. | |
| 9,375,338 B2 | 6/2016 | Baker et al. | |
| 9,414,948 B2 | 8/2016 | Baker et al. | |
| 9,545,326 B2 | 1/2017 | Baker et al. | |
| 9,549,833 B2 | 1/2017 | McHugo | |
| 9,629,733 B2 | 4/2017 | Roeder et al. | |
| 2001/0020189 A1 | 9/2001 | Taylor | |
| 2002/0032487 A1 | 3/2002 | Dua et al. | |
| 2002/0091395 A1 | 7/2002 | Gabbay | |
| 2003/0040804 A1 | 2/2003 | Stack et al. | |
| 2003/0040808 A1 | 2/2003 | Stack et al. | |
| 2003/0065359 A1 | 4/2003 | Weller et al. | |
| 2003/0109935 A1 | 6/2003 | Geitz | |
| 2003/0199989 A1 | 10/2003 | Stack et al. | |
| 2003/0212450 A1 | 11/2003 | Schlick | |
| 2004/0044357 A1 | 3/2004 | Gannoe et al. | |
| 2004/0087976 A1 | 5/2004 | DeVries et al. | |
| 2004/0092892 A1 | 5/2004 | Kagan et al. | |
| 2004/0106987 A1 | 6/2004 | Palasis et al. | |
| 2004/0116999 A1 | 6/2004 | Ledergerber | |
| 2004/0117031 A1 | 6/2004 | Stack et al. | |
| 2004/0138761 A1 | 7/2004 | Stack et al. | |
| 2004/0143342 A1 | 7/2004 | Stack et al. | |
| 2004/0148034 A1 | 7/2004 | Kagan et al. | |
| 2004/0172141 A1 | 9/2004 | Stack et al. | |
| 2004/0210111 A1 | 10/2004 | Okada | |
| 2004/0220682 A1 | 11/2004 | Levine et al. | |
| 2005/0004582 A1 | 1/2005 | Edoga et al. | |
| 2005/0043683 A1 | 2/2005 | Ravo | |
| 2005/0080395 A1 | 4/2005 | Levine et al. | |
| 2005/0096728 A1 | 5/2005 | Ramer | |
| 2005/0125020 A1 | 6/2005 | Meade et al. | |
| 2005/0197715 A1 | 9/2005 | Kugler et al. | |
| 2005/0228504 A1 | 10/2005 | Demarais | |
| 2005/0245788 A1 | 11/2005 | Gerber | |
| 2005/0245957 A1 | 11/2005 | Starkebaum et al. | |
| 2005/0247320 A1* | 11/2005 | Stack .............. | A61B 17/0469 128/898 |
| 2005/0251165 A1 | 11/2005 | Vaughan et al. | |
| 2005/0251176 A1 | 11/2005 | Swanstrom et al. | |
| 2005/0283235 A1 | 12/2005 | Kugler et al. | |
| 2006/0020277 A1 | 1/2006 | Gostout et al. | |
| 2006/0036293 A1 | 2/2006 | Whitehurst et al. | |

(56) References Cited

U.S. PATENT DOCUMENTS

| | | |
|---|---|---|
| 2006/0064120 A1 | 3/2006 | Levine et al. |
| 2006/0074473 A1 | 4/2006 | Gertner |
| 2006/0089571 A1 | 4/2006 | Gertner |
| 2006/0142844 A1 | 6/2006 | Lowe et al. |
| 2006/0149307 A1 | 7/2006 | Durgin |
| 2006/0155375 A1 | 7/2006 | Kagan et al. |
| 2006/0161139 A1 | 7/2006 | Levine et al. |
| 2006/0190019 A1 | 8/2006 | Gannoe et al. |
| 2006/0247721 A1 | 11/2006 | Maschino et al. |
| 2006/0253131 A1 | 11/2006 | Wolniewicz, III |
| 2006/0253142 A1 | 11/2006 | Bjerken |
| 2006/0253191 A1 | 11/2006 | Salahieh et al. |
| 2006/0264699 A1 | 11/2006 | Gertner |
| 2006/0265082 A1 | 11/2006 | Meade et al. |
| 2007/0005147 A1 | 1/2007 | Levine et al. |
| 2007/0010866 A1 | 1/2007 | Dann et al. |
| 2007/0010875 A1 | 1/2007 | Trout et al. |
| 2007/0088428 A1 | 4/2007 | Teichman |
| 2007/0112409 A1 | 5/2007 | Wu et al. |
| 2007/0123994 A1 | 5/2007 | Ortiz et al. |
| 2007/0166396 A1 | 7/2007 | Badylak et al. |
| 2007/0179590 A1 | 8/2007 | Lu et al. |
| 2007/0198035 A1 | 8/2007 | Threlkeld |
| 2007/0208429 A1 | 9/2007 | Leahy |
| 2007/0233221 A1 | 10/2007 | Raju |
| 2007/0260112 A1 | 11/2007 | Rahmani |
| 2007/0276432 A1 | 11/2007 | Stack et al. |
| 2007/0293716 A1 | 12/2007 | Baker et al. |
| 2008/0015523 A1 | 1/2008 | Baker |
| 2008/0015618 A1 | 1/2008 | Sonnenschein et al. |
| 2008/0015633 A1 | 1/2008 | Abbott et al. |
| 2008/0065122 A1 | 3/2008 | Stack et al. |
| 2008/0065136 A1 | 3/2008 | Young |
| 2008/0215076 A1 | 9/2008 | Baker |
| 2008/0312678 A1 | 12/2008 | Pasricha |
| 2009/0138071 A1 | 5/2009 | Cheng et al. |
| 2009/0177215 A1 | 7/2009 | Stack et al. |
| 2009/0187230 A1 | 7/2009 | Dilorenzo |
| 2009/0240340 A1 | 9/2009 | Levine et al. |
| 2009/0248171 A1 | 10/2009 | Levine et al. |
| 2009/0270818 A1 | 10/2009 | Duke |
| 2010/0010298 A1 | 1/2010 | Bakos et al. |
| 2010/0030017 A1 | 2/2010 | Baker et al. |
| 2010/0063518 A1 | 3/2010 | Baker et al. |
| 2010/0114124 A1 | 5/2010 | Kelleher et al. |
| 2010/0114130 A1 | 5/2010 | Meade et al. |
| 2010/0198237 A1 | 8/2010 | Baker et al. |
| 2010/0256775 A1 | 10/2010 | Belhe et al. |
| 2010/0280313 A1 | 11/2010 | Gasche et al. |
| 2011/0004146 A1 | 1/2011 | Priplata et al. |
| 2011/0009690 A1 | 1/2011 | Belhe et al. |
| 2011/0092879 A1 | 4/2011 | Baker et al. |
| 2011/0264234 A1 | 10/2011 | Baker et al. |
| 2012/0083871 A1 | 4/2012 | Ryan |
| 2012/0089168 A1 | 4/2012 | Baker et al. |
| 2012/0095497 A1 | 4/2012 | Babkes et al. |
| 2012/0191213 A1 | 7/2012 | Baker et al. |
| 2012/0191215 A1 | 7/2012 | Baker et al. |
| 2012/0203061 A1 | 8/2012 | Birk |
| 2012/0289991 A1 | 11/2012 | Baker |
| 2012/0310327 A1 | 12/2012 | McHugo |
| 2013/0123811 A1 | 5/2013 | Baker et al. |
| 2013/0296913 A1 | 11/2013 | Foote et al. |
| 2013/0324902 A1 | 12/2013 | Miller et al. |
| 2014/0018611 A1 | 1/2014 | Baker et al. |
| 2014/0114230 A1 | 4/2014 | Baker et al. |
| 2014/0121585 A1 | 5/2014 | Baker et al. |
| 2014/0277341 A1 | 9/2014 | Havel et al. |
| 2014/0309681 A1 | 10/2014 | Baker et al. |
| 2015/0025313 A1 | 1/2015 | Baker et al. |
| 2015/0039092 A1 | 2/2015 | Baker et al. |
| 2015/0182239 A1 | 7/2015 | Baker et al. |
| 2016/0038325 A1 | 2/2016 | Baker et al. |
| 2016/0151233 A1 | 6/2016 | Baker et al. |
| 2016/0228268 A1 | 8/2016 | Hingston et al. |
| 2016/0262867 A1 | 9/2016 | Baker et al. |
| 2016/0324671 A1 | 11/2016 | Baker et al. |
| 2017/0172723 A1 | 6/2017 | Foote et al. |

FOREIGN PATENT DOCUMENTS

| | | |
|---|---|---|
| EP | 2240215 B1 | 1/2014 |
| JP | 2660101 | 6/1997 |
| JP | 2006-103873 A | 4/2006 |
| JP | 2007508053 A | 4/2007 |
| JP | 2011509758 A | 3/2011 |
| RU | 2045233 C1 | 10/1995 |
| RU | 94026119 A | 8/1996 |
| RU | 2386455 | 4/2010 |
| WO | WO 93/22986 | 11/1993 |
| WO | WO 94/12136 | 6/1994 |
| WO | WO 01/35834 A1 | 5/2001 |
| WO | WO 01/85034 A1 | 11/2001 |
| WO | WO 02/060328 A1 | 8/2002 |
| WO | WO 02/094105 A2 | 11/2002 |
| WO | WO 2004/019826 A1 | 3/2004 |
| WO | WO 2004/064680 A1 | 8/2004 |
| WO | WO 2004/064685 | 8/2004 |
| WO | WO 2005/037152 A1 | 4/2005 |
| WO | WO 2006/044640 A1 | 4/2006 |
| WO | WO 2006/078672 A1 | 7/2006 |
| WO | WO 2007/092390 A2 | 8/2007 |
| WO | WO 2008/100984 A2 | 8/2008 |
| WO | WO 2008/101048 A2 | 8/2008 |
| WO | WO 2008/101078 A2 | 8/2008 |
| WO | WO 2009/048398 A1 | 4/2009 |
| WO | WO 2009/091899 A2 | 7/2009 |
| WO | 2010117641 A2 | 10/2010 |
| WO | WO 2011/056608 A1 | 5/2011 |
| WO | WO 2011/063307 A1 | 5/2011 |
| WO | WO 2011/089601 A1 | 7/2011 |
| WO | WO 2011/097209 A1 | 8/2011 |
| WO | WO 2011/116025 A1 | 9/2011 |
| WO | WO 2012/044917 A1 | 4/2012 |
| WO | 2012136249 A1 | 10/2012 |
| WO | WO 2012/162114 A1 | 11/2012 |
| WO | WO 2013/090190 A1 | 6/2013 |
| WO | WO 2013/134227 A1 | 9/2013 |
| WO | WO 2014/141239 A1 | 9/2014 |
| WO | WO 2015/031077 A1 | 3/2015 |
| WO | WO 2016/109346 A1 | 7/2016 |

OTHER PUBLICATIONS

International Preliminary Report on Patentability and Written Opinion of the International Searching Authority from corresponding Patent Cooperation Treaty (PCT) Patent Application No. PCT/US12/38480, dated Nov. 29, 2013.

"Obesity: Super-Sized Medical Device Market", Start-Up, Mar. 2003, Technology Strategies (Long Article), pp. 1-10 and a cover page.

Andrew S. Lowe, M.D. and Maria B. Sheridan, M.D., "Esphogeal Stenting", Seminars in Interventional Radiology, vol. 21, No. 3, 2004, pp. 157-166.

"Polyflex® Espohageal Stent", Silicone Covered Stent, Boston Scientific, three pages (2003).

Andrew F.R. Dixon, Johgn B. Dixon, and Paul E. O'Brien, "Laparoscopic Adjustable Gastric Banding Induces Prolonged Satiety: A Randomized Blind Crossover Study", The Journal of Clinical Endocrinology & Metabolism , pp. 813-819, 2005.

Roman, S. et al., "Intragastric balloon for 'non-morbid' obesity: a retrospective evaluation of tolerance and efficacy," Obes. Surg., 2004, 14(4), 539-44, abstract, [on-line], [found Apr. 17, 2009, from Pubmed database].

Busetto, L. et al., "Preoperative weight loss by intragastric balloon in super-obese patients treated with laparoscopic gastric banding: a case-control study," Obes Surg., 2004, 14(5), 671-6, abstract, [on-line], [found Apr. 17, 2009, from Pubmed database].

Summary of Official Action dated Oct. 29, 2009, from the Israel Patent Office in a patent application corresponding to the present application.

(56) References Cited

OTHER PUBLICATIONS

Lowe, Andrew S., M.D. and Sheridan, Maria B., M.D., "Esophageal Stenting," annotated by Israel Patent Office (2004).
Abstract and claims of U.S. Pat. No. 6,960,233 annotated by the Israel Patent Office (Nov. 1, 2005).
Schembre, Drew, "Advances in Esophageal Stenting: the Evolution of Fully Covered Stents for Malignant and Benign Disease," Adv. Ther., Springer Healthcare, Apr. 1, 2010, pp. 1-13.
International Preliminary Report on Patentability and Written Opinion of the International Searching Authority from corresponding Patent Cooperation Treaty (PCT) Patent Application No. PCT/US08/53912, completed Aug. 19, 2009.
International Preliminary Report on Patentability and Written Opinion of the International Searching Authority from corresponding Patent Cooperation Treaty (PCT) Patent Application No. PCT/US05/36991, completed Mar. 6, 2006.
S. Fukudo, T. Nomura, M. Hongo, "Impact of corticotropin-releasing hormone on gastrointestinal motility and adrenocorticotropic hormone in normal controls and patients with irritable bowel syndrome", Jan. 19, 1998.
D.G. Maxton, D.F. Martin, P.J. Whorwell, M. Godfrey. "Abdominal distension in female patients with irritable bowel syndrome: exploration of possible mechanisms", Aug. 3, 1990.

\* cited by examiner

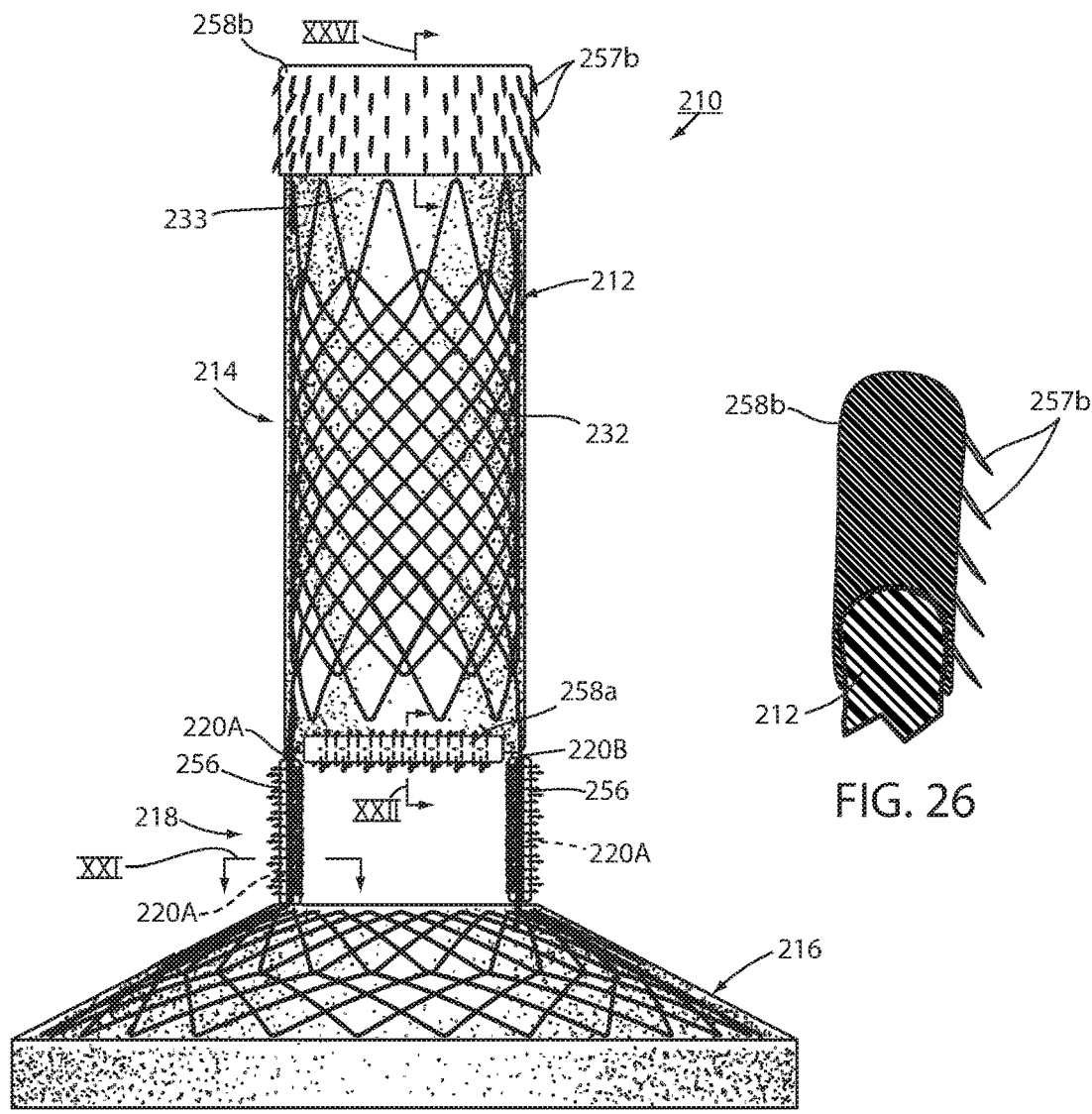
FIG. 19
FIG. 26
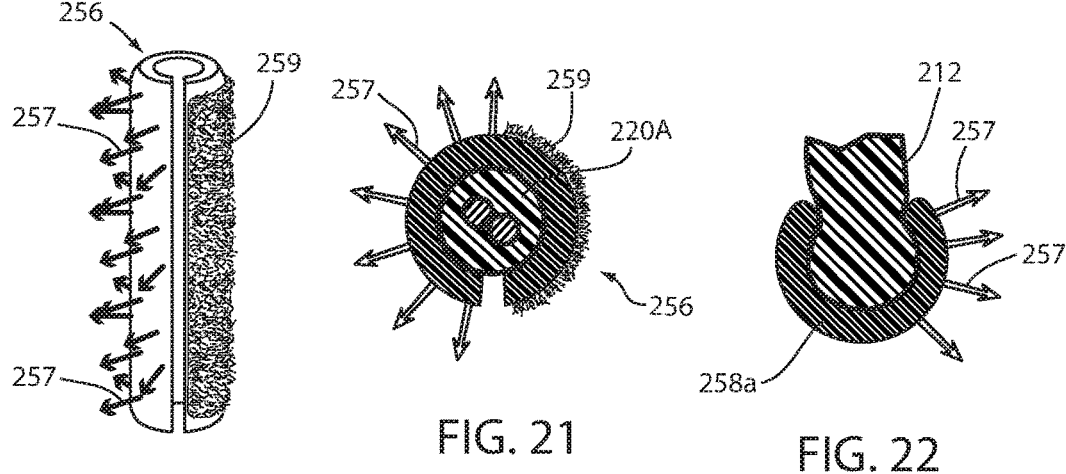
FIG. 20
FIG. 21
FIG. 22

FIXATION OF INTRALUMINAL DEVICE

BACKGROUND OF THE INVENTION

The present invention is directed to an intraluminal device and method of fixation of an intraluminal device and, in particular, a technique that enhances both fixation and removeability of the device. While the invention is illustrated for use with a bariatric device and/or a metabolic device, it may be applied to other intraluminal devices positioned in a mammalian lumen or hollow organ that is subject to peristalsis, such as an esophageal stent, an anti-reflux device, a nasal gastric tube, an intestinal sleeve, and the like, including devices positioned in the fallopian tubes, vas deferens, and the like.

SUMMARY OF THE INVENTION

An intraluminal device and method of providing satiety and/or treating a metabolic disease in a recipient is disclosed in commonly assigned U.S. Pat. Nos. 7,846,174; 8,100,931; 8,372,087; 8,529,431; 8,672,831; 8,801,599; 8,894,670 and 9,055,998 and International Publications Nos. WO2012/044917; WO2012/162114; WO2013/134227 and WO 2015/031077, the disclosures of which are hereby collectively incorporated herein by reference in their entirety. Such devices and methods apply stress to the gastro-intestinal tract in general and in particular to the cardiac portion of the stomach of the recipient to produce satiety in the absence of food and to augment fullness caused by food and/or to treat a metabolic disease. A challenge with such devices and methods is fixation of a portion of the device against a surface of the GI tract, such as the cardiac portion of the stomach in the presence of peristalsis tending to cause distal migration of the device.

While the use of tissue ingrowth patented in the above-identified patents has been found to provide a satisfactory solution for fixation to resist distal migration, aspects of the present invention includes providing short-term fixation of the device until the tissue ingrowth providing long-term fixation is in place. Such short-term fixation is easy to carry out and capable of complete fixation over the days or weeks that it takes for the long-term fixation to occur.

Aspects of the present invention provide techniques for explanation of an intraluminal device having a wall defining first and second wall portions configured to be positioned in a lumen. The first wall portion may be an esophageal portion that is configured to the size and shape of a portion of the esophagus. The second wall portion may be a cardiac portion that is configured to the size and shape of the cardiac portion of the stomach. A connector connecting the esophageal and cardiac portions is positioned against lumen tissue, such as in the gastroesophageal (GE) junctions wherein lumen tissue bridges or encases the connector during deployment of the device. Explanation of the device should not substantially damage the GE junction of the recipient. Aspects of the present invention facilitate such explanation and provide techniques that may beneficially utilize such tissue bridging the connector for long-term fixation of an intraluminal device.

An intraluminal device adapted to be positioned in a lumen, according to an aspect of the invention, includes a wall having a first wall portion configured to the size and shape of a first portion of the lumen and a second wall portion configured to the size and shape of a second portion of the lumen. A connector is connected with the first wall portion with the second wall portion. The connector is configured to be positioned against the lumen and wherein the connector is separably connected with one or both of the first and second wall portions. This allows the device to be explanted by disconnecting the connector and axially withdrawing the connector from tissue that encases the connector without substantial damage to the tissue.

The wall portions may be joined with the connector prior to deployment in the lumen. The connector may include at least one filament that is coated with a bio-compatible material that extends around the at least one filament from one of the wall portions to the other of the wall portions. A removable attachment may connect the connector with at least one of the wall portions and wherein the connector is separable by removing the removable attachment. The removable attachment may include a severable filament.

The device may include a fixation system that is configured to resist distal migration of the wall in the lumen. The fixation system may include the connector having a configuration to facilitate tissue of the lumen growing around the connector. The fixation system may include a tissue penetrating fastener configured to engage the connector with tissue of the lumen. The connector may include at least one elongated member including irregular portions thereof.

The fixation system may include a long-term fixation system including a characteristic of the wall that is configured to facilitate tissue adhesion to the wall and a temporary fixation system that at least initially resists distal migration of the wall, wherein the temporary fixation system includes a tissue penetrating fastener. The temporary fixation system may include a looped filament extending from that at least one of the wall portions and is configured to be captured with the fastener. The looped filament may be at least partially elastic and may be at least partially bioabsorbable.

The intraluminal device may be an esophageal stent, an anti-reflux device, a nasal gastric tube, an intestinal sleeve, a bariatric device or a metabolic disease treatment device.

An intraluminal device adapted to be positioned at the gastro-esophageal (GE) region of a recipient, according to an aspect of the invention, includes a wall defining an esophageal portion that is configured to the size and shape of a portion of the esophagus and a cardiac portion that is configured to the size and shape of the cardiac portion of the stomach. A connector is connected with said esophageal and cardiac portions and configured to be positioned at the GE junction. The connector is separably connected with the esophageal portion and/or the cardiac portion.

The connector may be separably connected with the wall with a removable attachment. A separable portion of the connector may extend along the wall and the removable attachment may be a severable filament between the separable portion and the wall. The wall may include a structural mesh defining intersections and covered with a biocompatible coating and the separable portion of the connector includes one or more openings defined by the connector that align with one or more intersections of the mesh wherein the severable filament extends between the opening(s) and the intersection(s). A plurality of openings and intersections may be aligned and the severable filament formed as a chain stitch between the openings and intersections.

The wall may include a structural mesh defining intersections and covered with a biocompatible coating with a separable portion of the connector extending over one or more intersections and under one or more intersections. The removable attachment is between the separable portion and the mesh keeping the connector from sliding with respect to the intersections. The removable attachment may be a filament between said distal portion and the mesh. A bead may be provided on the filament to provide access to the filament. The connector may extend over a plurality of intersections and under at least one intersection that is between the plurality of intersections.

The connector may include a filament and a biocompatible coating over the filament. The connector may include a therapeutic agent eluting coating. A therapeutic agent dispensing reservoir may be at a distal portion of the esophageal portion that is adapted to dispense a therapeutic agent to the connector. The device may be a bariatric device used to treat excess body mass or a metabolic device used to treat metabolic disease.

An intraluminal device adapted to be deployed at the gastroesophageal (GE) region of a recipient, according to an aspect of the invention, includes a wall defining a cardiac portion that is configured to the size and shape of the cardiac portion of the stomach, an esophageal portion that is configured to the size and shape of a portion of the esophagus and a connector connected with said esophageal portion and said cardiac portion. A fixation system is configured to resist distal migration of the wall and includes short-term fixation and long-term fixation. The long-term fixation includes a characteristic of the wall that is configured to facilitate tissue ingrowth. The short-term fixation at least temporarily resists distal migration of the wall while tissue grows to the wall as the characteristic. The long-term fixation and short-term fixation are at least partially at the connector.

The characteristic of the wall may include the connector being an elongated filament. The characteristic of the wall may be a tissue ingrowth promotion surface configuration of the connector. The tissue ingrowth promotion surface configuration may face inwardly away from the GE junction.

The short-term fixation may include a tissue penetrating fastener that fixes the device at least partially at the GE junction. The tissue penetrating fastener may face outwardly toward the GE junction. The tissue penetrating fastener may engage the GE junction as a function of deployment of the device at the GE region of the recipient. The tissue penetrating fastener may be applied to tissue at the connector after deployment of the device at the GE region of the recipient. The tissue penetrating fastener may be positioned in part at the esophageal portion. The tissue penetrating fastener positioned in part at the esophageal portion may be configured to penetrate the tissue of the lumen upon deployment of the device. The tissue penetrating fastener may be made at least in part from a bio-absorbable material.

The connector may include a filament and a biocompatible coating over the filament. The connector may include a therapeutic agent eluting coating. A therapeutic agent dispensing reservoir may be at a distal portion of the esophageal portion that is adapted to dispense a therapeutic agent to the connector. The device may be a bariatric device used to treat excess body mass or a metabolic device used to treat metabolic disease.

An intraluminal device adapted to be deployed at the gastroesophageal (GE) region of a recipient, according to an aspect of the invention, includes a wall defining a cardiac portion that is configured to the size and shape of the cardiac portion of the stomach, an esophageal portion that is configured to the size and shape of a portion of the esophagus and a connector connected with said esophageal portion and said cardiac portion. A fixation system is configured to resist distal migration of said wall. The fixation system includes short-term fixation and long-term fixation. The long-term fixation includes a characteristic of the wall that is configured to facilitate tissue ingrowth. The short-term fixation is configured to at least temporarily resist distal migration of the wall while tissue grows to said wall as said characteristic. The short-term fixation includes a tissue penetrating fastener.

The short-term fixation may include a looped filament extending proximally from at least the esophageal portion that is configured to be captured by the tissue penetrating fastener. The looped filament may be made at least in part of an elastic material and/or a bioabsorbable material. An enlarged portion of the looped filament may be provided wherein the fastener penetrates tissue and the enlarged portion. A retainer filament may be provided that is temporarily connected with the looped filament. The retainer filament extends from the esophagus for use with positioning the wall at the GE junction of the recipient. The retainer filament may be removed after deployment of the device.

The tissue penetrating fastener may include a suture. The tissue penetrating fastener may include barbs on the wall and facing the GE region. The barbs engage the tissue of the GE region upon deployment of the device. The barbs may be formed on the wall. The barbs may be formed on a separate fastener attached with the wall or formed on the wall. The fastener may be at least partially made with a bio-absorbable material. A tissue attachment surface may be provided on the tissue penetrating fastener opposite the barbs to attach tissue drawn around the connector. The temporary fixing may provide diminishing resistance of distal migration after long-term fixing of the wall to the GE region has at least partially occurred. The wall characteristic may include tissue ingrowth openings in the wall. A therapeutic drug eluting coating may be provided at the openings in the wall.

The device may be a bariatric device used to treat excess body mass or a metabolic device used to treat metabolic disease.

A method of deployment of an intraluminal device to resist distal migration in a mammalian lumen or hollow organ that is subject to peristalsis, according to an aspect of the invention, wherein the intraluminal device includes spaced apart wall portions connected with a connector. The wall portions are configured to the size and shape of a portion of the lumen or hollow organ and the connector is configured to be positioned against a wall of the lumen or hollow organ. The intraluminal device is positioned in a mammalian lumen or hollow organ that is subject to peristalsis. The device is fixed in the lumen or hollow organ against distal migration, wherein tissue lining the lumen or hollow organ bridges over the connector. The device is explanted after tissue bridges over the connector including separating the connector from one or both of the wall portions and withdrawing the connector axially from the tissue bridging over the connector.

A method of deployment of an intraluminal device at the gastroesophageal (GE) region of the recipient to resist distal migration, the device having a wall defining an esophageal portion that is configured to the size and shape of a portion of the esophagus, a cardiac portion that is configured to the size and shape of the cardiac portion of the stomach and a connector connected with the esophageal and cardiac portions, according to an aspect of the invention, includes positioning the device at the GE region with the esophageal portion in the esophagus, the cardiac portion at the cardiac portion of the stomach and at least a portion of said connector at the gastroesophageal (GE) junction, wherein tissue at the GE junction at least partially encompasses the connector. The device is explanted after tissue has encompassed the connector including separating the connector from the esophageal portion and/or the cardiac portion and withdrawing the connector axially from the tissue encompassing the portion of the connector at the gastroesophageal junction.

A method of deployment of an intraluminal device at the gastroesophageal (GE) region of a recipient to resist distal migration, the device having a wall defining a cardiac portion that is configured to the size and shape of the cardiac portion of the stomach, an esophageal portion that is configured to the size and shape of a portion of the esophagus and a connector connected with the esophageal portion and the cardiac portion, according to an aspect of the invention, includes positioning the device at the GE region with the esophageal portion in the esophagus, the cardiac portion at the cardiac portion of the stomach and at least a portion of said connector at the gastroesophageal (GE) junction. Short-term fixation and long-term fixation of the device positioned at the GE region are provided. The long-term fixation includes a characteristic of the wall that is configured to facilitate tissue ingrowth. The short-term fixation at least temporarily resisting distal migration of said wall while tissue grows to the wall characteristic. The providing of long-term fixation includes positioning the device with a characteristic of the wall that is configured to facilitate tissue ingrowth positioned at the GE junction. The providing of short-term fixation includes temporarily fixing the device at least partially at the GE junction.

A method of deployment of an intraluminal device at the gastroesophageal (GE) region of a recipient, the device having a wall defining a cardiac portion that is configured to the size and shape of the cardiac portion of the stomach, an esophageal portion that is configured to the size and shape of a portion of the esophagus and a connector connected with the esophageal portion and the cardiac portion, according to an aspect of the invention, includes positioning the device at the GE region with the esophageal portion in the esophagus, the cardiac portion at the cardiac portion of the stomach and at least a portion of said connector at the gastroesophageal (GE) junction. Short-term fixation and long-term fixation of the device is positioned at the GE region. The long-term fixation includes a characteristic of said wall that is configured to facilitate tissue ingrowth. The short-term fixation at least temporarily resists distal migration of the wall while tissue grows to said wall characteristic. The long-term fixation is provided including positioning the device with a characteristic of said wall that is configured to facilitate tissue ingrowth positioned against the lumen. The short-term fixation is provided including temporarily fixing the device in the lumen to at least temporarily resist distal migration of the wall while tissue grows to said wall as the characteristic including fixing the device with a tissue penetrating fastener.

These and other objects, advantages, purposes and features of the present invention will become apparent upon review of the following specification in conjunction with the drawings.

BRIEF DESCRIPTION OF THE DRAWINGS

FIG. 19 is a side elevation of an alternative embodiment of a bariatric device;
FIG. 20 is a perspective view of a retainer that is capable of short-term fixation and facilitating long-term fixation;
FIG. 21 is a sectional view taken along the lines XXI-XXI in FIG. 19;
FIG. 22 is a sectional view taken along the lines XXII-XXII in FIG. 19;
FIG. 26 is a sectional view taken along the lines XXVI-XXVI in FIG. 19.

DESCRIPTION OF THE PREFERRED EMBODIMENTS

Figure 1:
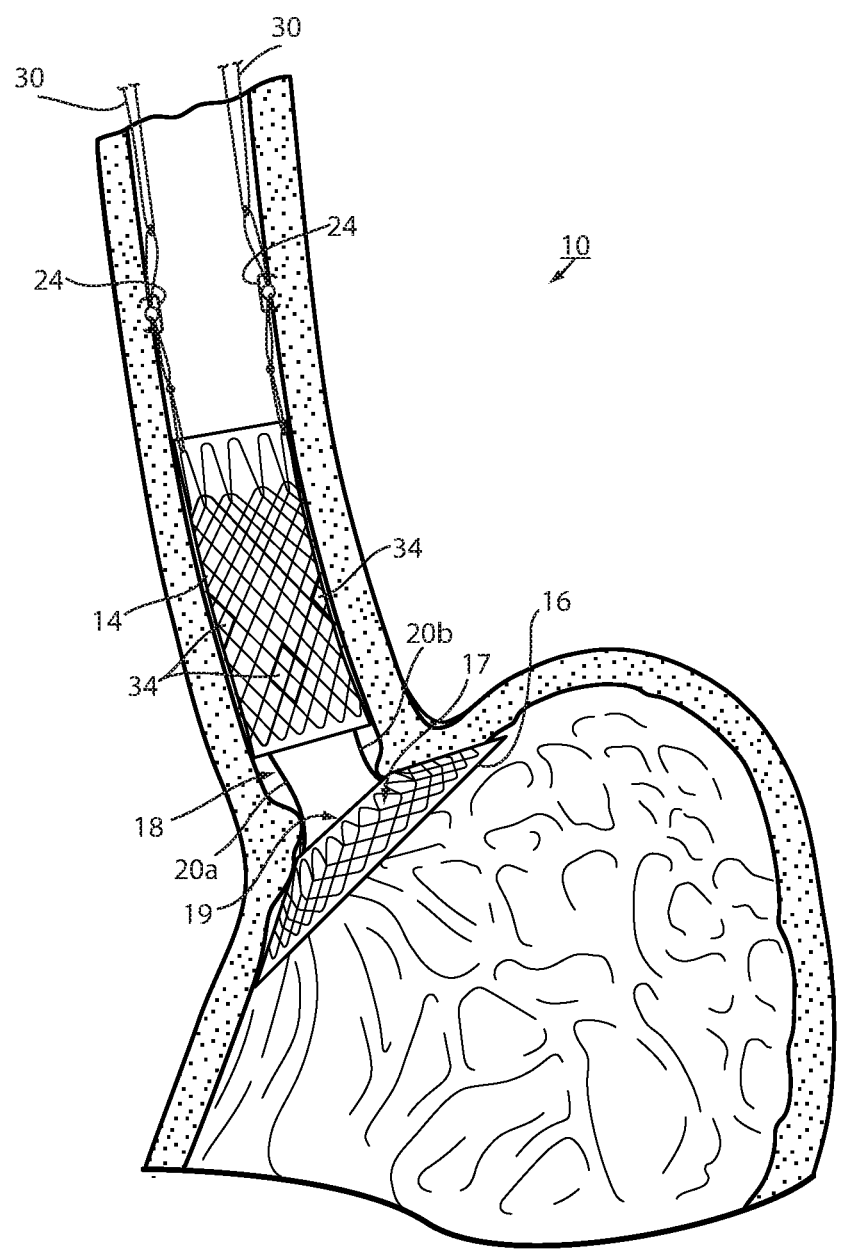
FIG. 1 is a cross section of an intraluminal device deployed in a mammalian lumen or hollow organ of a recipient, namely, a bariatric device at the gastroesophageal (GE) region of the recipient.

Referring now to the drawings and the illustrative embodiment depicted therein, an intraluminal device, such as a bariatric device or a metabolic disease treatment 10, has a wall 12 defining an esophageal portion 14 that is configured to the size and shape of a portion of a mammalian lumen or hollow organ, namely, the esophagus, a cardiac portion 16 that is configured to the size and shape of a separated portion of mammalian lumen or hollow organ, namely, the cardiac portion of the stomach and a connector 18 connecting esophageal portion 14 and cardiac portion 16 (FIGS. 1-5). While illustrated as a bariatric device, it should be understood that that principles of the invention are applicable to other intraluminal devices that are positioned in a lumen or hollow organ that experiences peristalsis, such as an esophageal stent, an anti-reflux device, a nasal gastric tube, an intestinal sleeve, and the like. Also, the invention may be applied to a metabolic disease treatment device and method as disclosed in commonly assigned International Patent Application Publication No. WO 2015/031077 A1, the disclosure of which is hereby incorporated by reference in its entirety.

Figure 2:
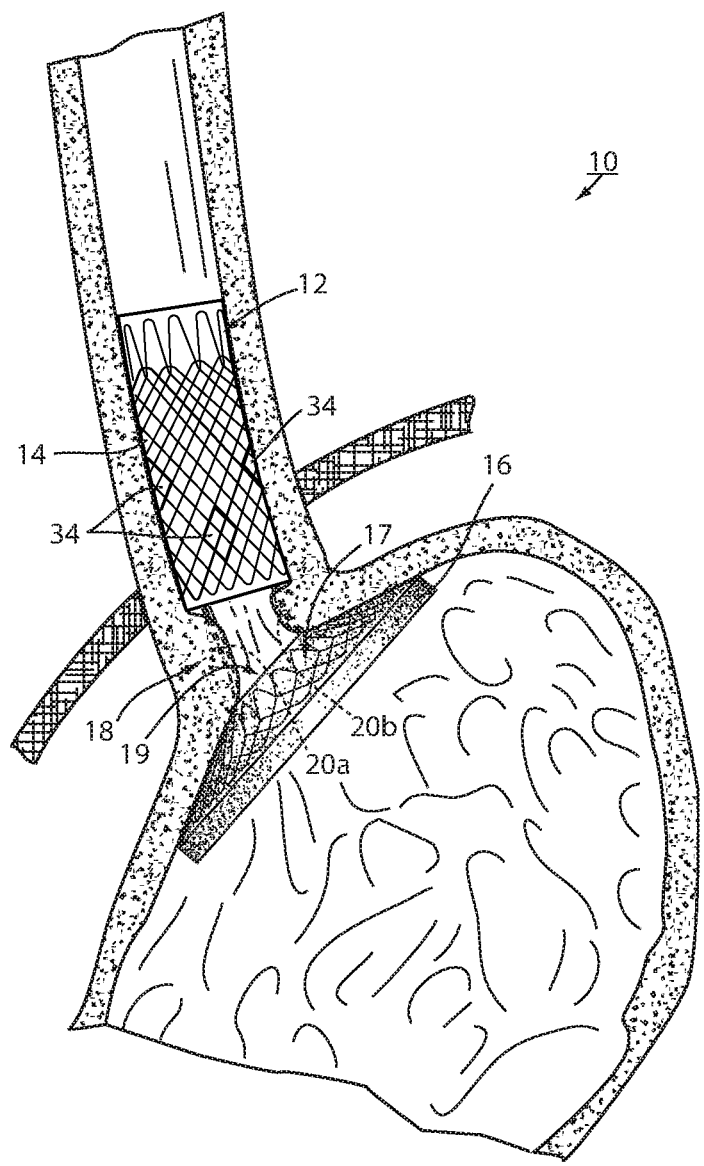
FIG. 2 is the same view as FIG. 1 after the device has been deployed at the GE region for a period of time, such as several weeks or months.

As can be seen in FIGS. 1 and 2, intraluminal device 10 is positioned at the gastroesophageal region with the esophageal portion 14 in the esophagus, the cardiac portion 16 at the cardiac portion of the stomach and at least a portion of connector 18 extending through the gastroesophageal (GE) junction. In the illustrated embodiment, connector 18 is made up of two elongated filaments 20a, 20b which are in tension and may be referred to as struts. As can be seen by comparing FIGS. 1 and 2, with device 10 fixed at the gastroesophageal region to cause body mass loss, mucosa (which may include submucosa and even musculara) tissue bridges over at least one of the two struts 20a, 20b as shown in FIG. 2 after device 10 has been positioned in the GE region. The bridging tissue can fuse with time sufficiently to achieve significant loss of excess body mass making it difficult to explant intraluminal device 10. Also, as will be discussed in more detail below, tissue bridging of struts 20a, 20b may provide long-term fixation of device 10, alone or in combination with other functions in accordance with the principles set forth in commonly assigned U.S. Pat. No. 8,894,670 B2. In particular, the struts correspond to the bridge in the '670 patent and the spaces between the struts correspond to the openings adjacent the bridge in the '670 patent so that the tissue bridging over the struts implements mucosal capture patented in the '670 patent.

Fixation of intraluminal device 10 against distal migration includes a fixation technique 22 that fastens esophageal portion 14 with the esophagus with a fastener such as a tissue penetrating fastener 24. A looped filament 26 extending proximally from esophageal portion 14 is captured with fastener 24 engaging the wall of the esophagus by the fastener. The loops in the looped filament are positively engaged by the fastener so that the esophageal portion 14 is firmly fixed to the esophagus by the fastener. The number of loops can vary from one to many and can be any size or shape as long as they are a closed polygon. In the illustrated embodiment, fastener 24 is an endoscopically deployed clip marketed by Ovesco and described in detail in U.S. Pat. No. 8,721,528 for an ENDOSCOPE CAP, the disclosure of which is hereby incorporated herein by reference. Also, although two loops and penetrating fasteners are illustrated, one or more than two may be used.

Figure 4:
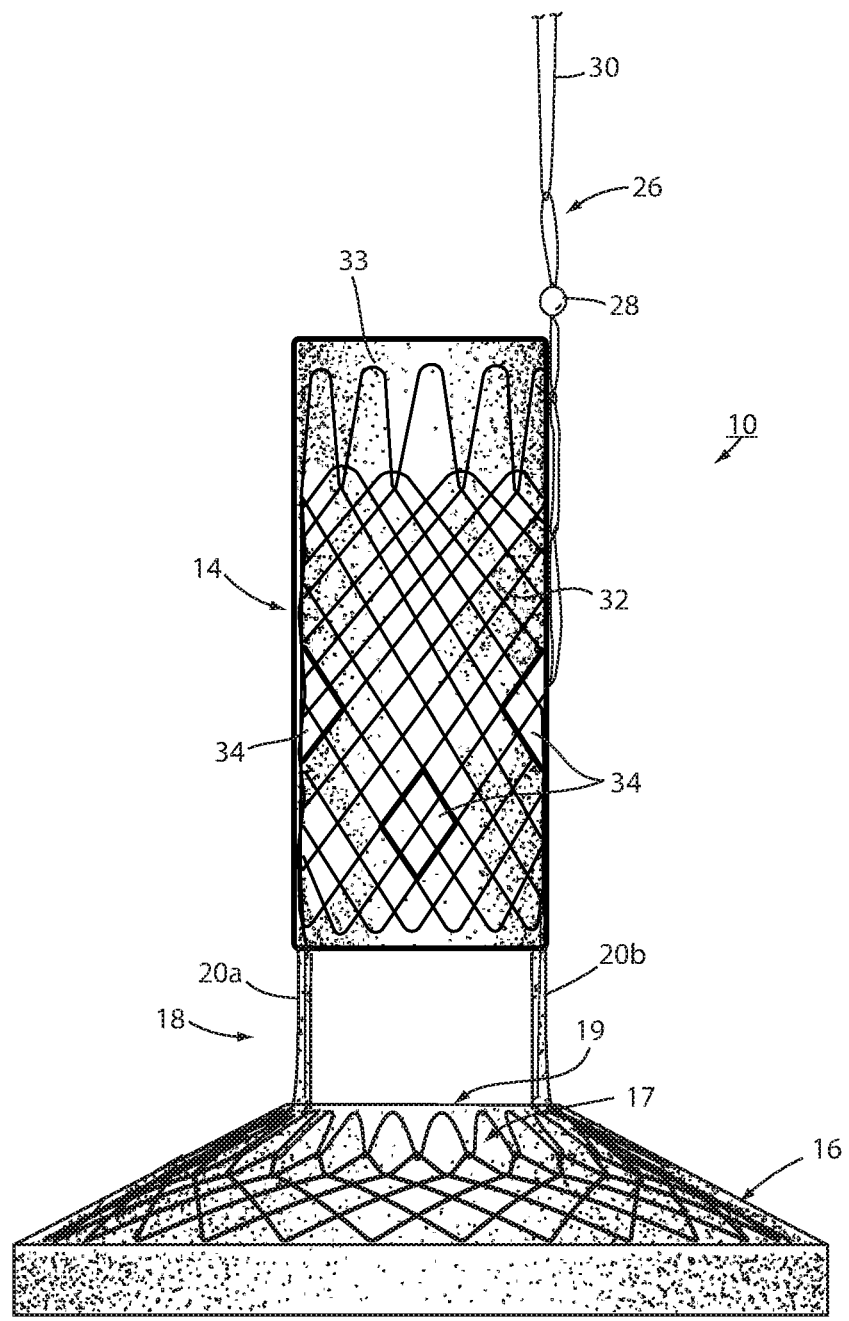
FIG. 4 is the same view as FIG. 3 of an alternative embodiment thereof.

Fixation technique 22 is intended to provide at least temporary fixation to maintain device 10 in position at the GE region of the recipient with cardiac portion 16 engaging the cardiac region of the stomach while permanent fixation develops. Looped filament 26 may be at least partially elastic in order to be slightly stretched when fastener 24 is deployed to maintain upward pressure on cardiac portion 16 after deployment. Looped filament 26 may be at least partially bioabsorbable, or resorbable, so that it, along with fastener 24, may fall away after permanent fixation occurs as seen in FIG. 2. Looped filament 26 may be made from monofilament or braided filament. An enlarged portion 28 of filament 26 may be provided and fastener 24 applied at or adjacent tissue of the esophageal wall that is drawn over the enlarged portion 28 by suction. Alternatively, the fastener 24 may be applied adjacent the enlarged portion 28, such as distal the enlarged portion. The enlarged portion and the loops defining looped filament 26 provide engagement between the mechanical fastener and the looped filament to prevent the looped filament from pulling away from the fastener. In the illustrated embodiment, enlarged portion 28 is a bead. As illustrated in FIG. 4, it may be desirable to position enlarged portion 28 as close as possible to esophageal member 14 to avoid entanglement between a retainer filament 30 discussed below and another retainer filament (not shown) that extends proximally from esophageal member 14.

A retainer filament 30 may be temporarily connected with the looped filament 26 and extending external the recipient of the device from the esophagus. Retainer filament 30 allows the physician or other healthcare worker the ability to position bariatric device 10 properly at the GE region and to apply tension to looped filament 26 until fastener 24 is applied. As retainer filament 30 is merely looped proximally to looped filament 26, it can be easily retraced by pulling on one side of the loop. Looped filament 26 is connected directly with the mesh 32 that provides a structure to bariatric device 10. This allows the looped filament to apply proximal axial force to mesh which force is then distributed over wall 12 without causing a narrowing of esophageal portion 14 as may occur if the looped filament were to be connected with a removal suture (not shown) that encircles esophageal portion 14 proximally and is used to remove device 10. If a proximal force were to be applied to such removal suture, the diameter of esophageal portion 14 may be reduced upon fixation thus counteracting mucosal capture and/or tissue ingrowth of the wall of the esophageal portion to the esophageal wall. While the application of proximal axial force to such removal suture, or ring, may be a useful action to explant intraluminal device 10, it would not be useful in providing fixation.

Figure 3:
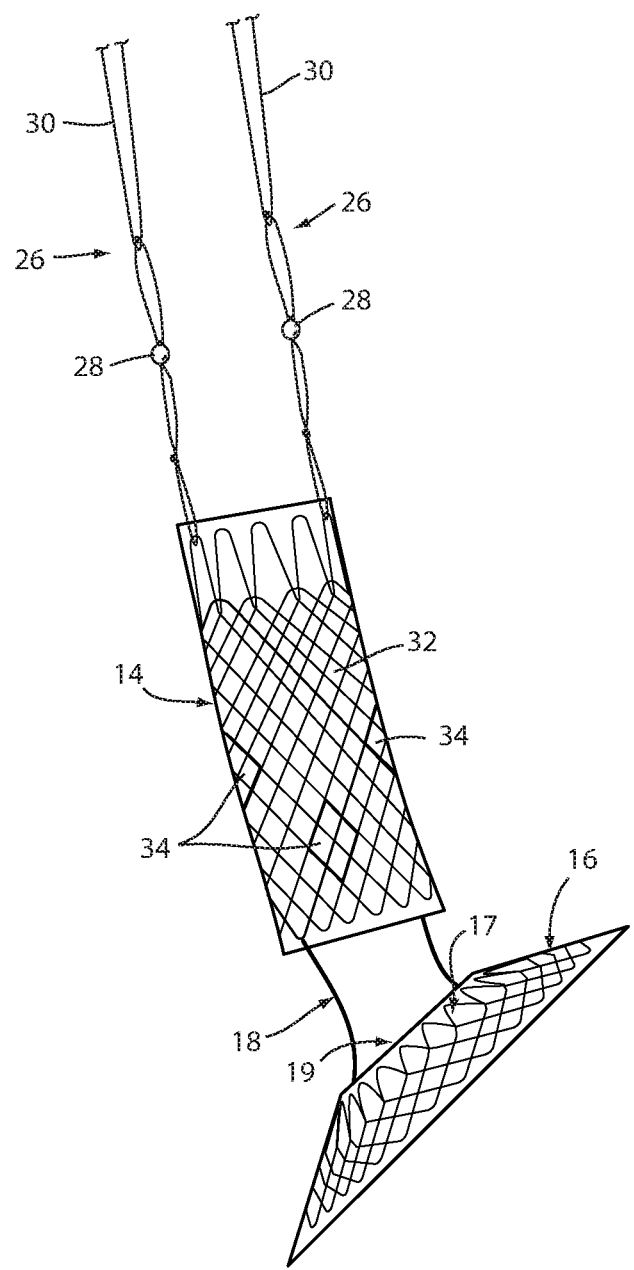
FIG. 3 is a side elevation of the device in FIGS. 1 and 2.

Thus, the direct connection of looped filament 26 to mesh 32 allows proximal axial force to be applied to esophageal portion 14 without inducing a radially inward force tending to pull wall 12 away from the esophagus wall. While looped filament 26 is shown in FIG. 1 and FIG. 3 connected with a proximal end portion of mesh 32, it could also be connected at a central or distal portion of the mesh as shown in FIG. 4. While filament 26 could extend from the interior of esophageal portion 14, it could also extend from an outer surface of the esophageal member wall, as shown in FIG. 4, thereby ensuring that any tension force on filament 26 tends to pull the esophageal member wall toward the esophagus wall. Also, as shown in FIG. 4, cardiac portion 16 may include a transition zone 17 adjacent its proximal opening 19 in order to resist any irritation of the tissue of the cardiac portion of the stomach in accordance with the principles set forth in commonly assigned International Patent Application Publication No. WO 2012/044917, the disclosure of which is hereby incorporated herein by reference in its entirety.

Figure 6:
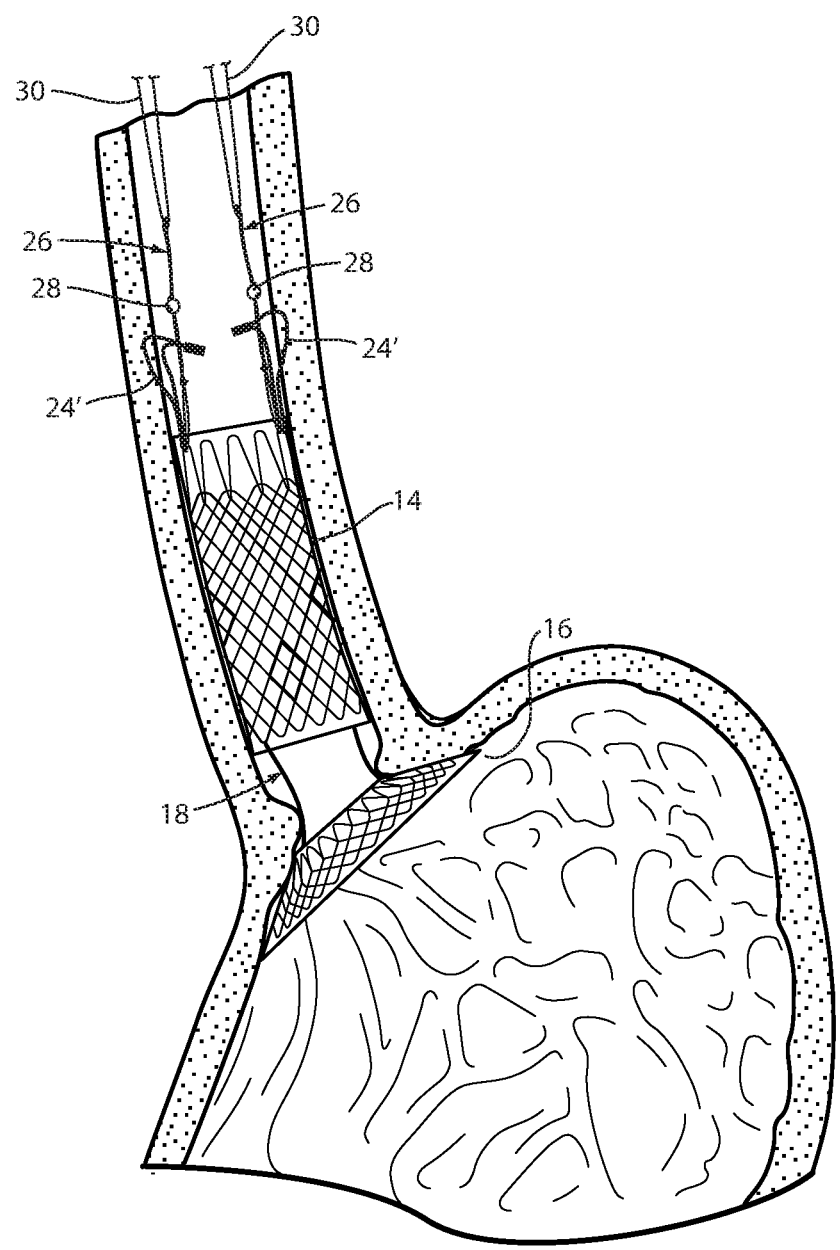
FIG. 6 is the same view as FIG. 1 showing an alternative short-term fixation of the device.

In an alternative technique illustrated in FIG. 6 temporary fixation is provided by a tissue penetrating fastener in the form of sutures 24'. Each suture 24' is passed through the wall of esophageal portion 14 and at least partially through the wall of the esophagus of the recipient. The suture may be applied endoscopically, such as by using an automated suture device that is commercially available such as one marketed by Apollo Endosurgery. The suture is preferably made from an absorbable material so that it dissolves over time as more permanent fixation from tissue capture takes over. In the embodiment used in FIG. 6, looped filament 26 is used to transmit the retaining force from retainer filament 30 to the esophageal member 14 but does not form a part of temporary fixation. It would be possible to attach retainer filament 30 directly to esophageal portion 14.

Fixation of device 10 against distal migration includes temporary fixing, such as using fixation 22, and long-term fixing from wall characteristics that fixes the wall to the GE region through growth of tissue, such as using tissue ingrowth zones 34 formed in wall 12.

Figure 5:
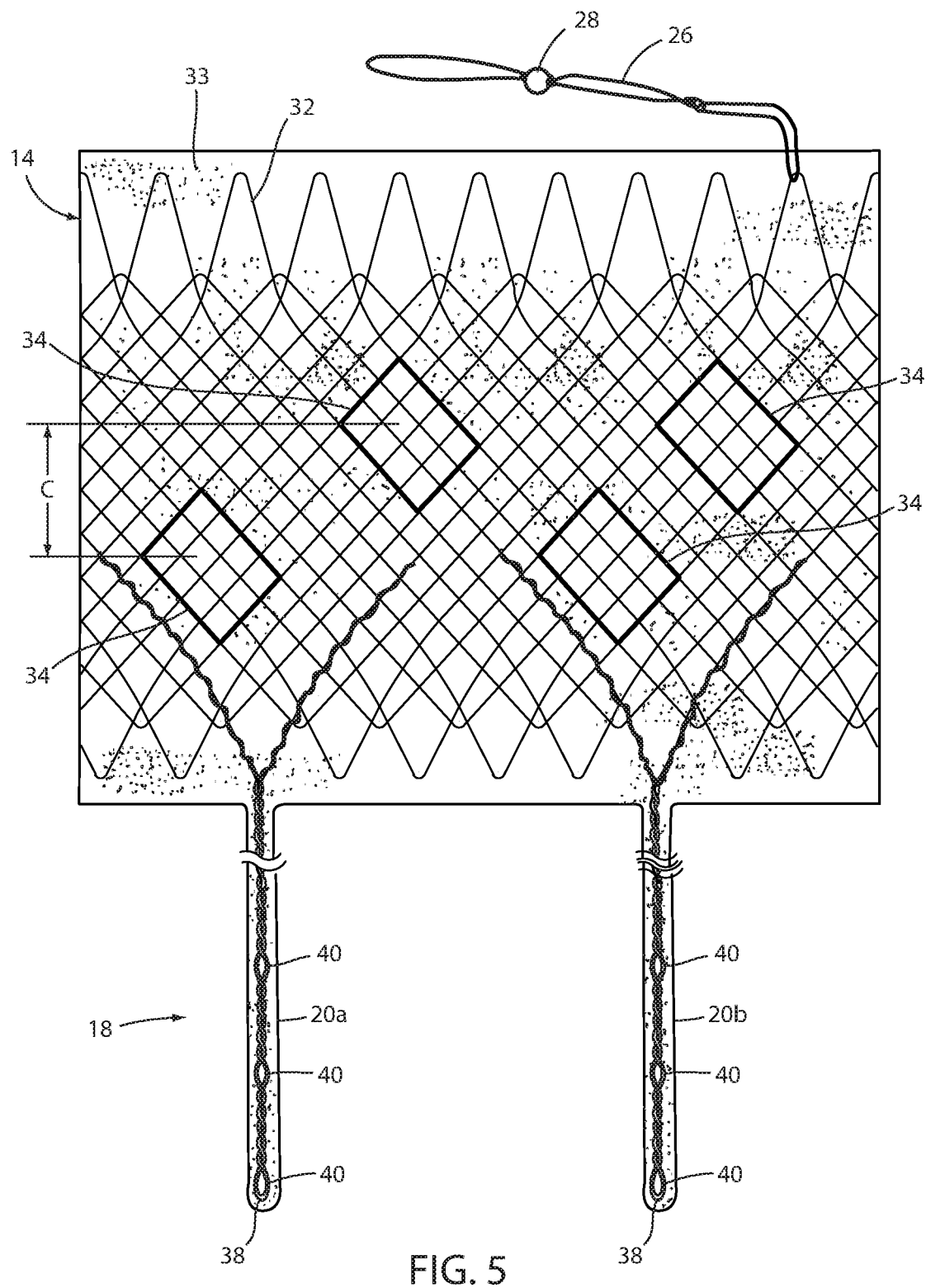
FIG. 5 is a plan view of the esophageal portion and connector portions of FIG. 3 with the esophageal portion unrolled into a flat state.

Tissue ingrowth zones 34 are openings in the cover 33 of biocompatible material, such as silicone, over mesh 32, which openings allow tissue to grow over members of the mesh. As shown in FIG. 5 and as disclosed in U.S. Pat. Application Publication No. 2014/0121585 entitled INTRALUMINAL DEVICE AND METHOD WITH ENHANCED ANTI-MIGRATION, the disclosure of which is hereby incorporated herein by reference, zones 34 are more effective if spaced apart a distance "C" in the direction of peristalsis on an order of magnitude of at least the wavelength of the peristaltic wave. Long-term fixation using ingrowth openings 34 may be removed to explant device 10, such as by cauterizing the tissue in the mucosal capture zones 34 and by placing an inward radial force on esophageal portion 14 such as by applying a proximal force on the removal suture (not shown) in order to remove device 10. Also, an overtube, of the type known in the art, may be inserted between esophageal portion 14 and the wall of the esophagus to further separate wall 12 from the tissue of the esophagus. Other techniques for removing mucosa from openings 34, such as mechanical severing of the tissue, will be apparent to the skilled artisan.

Tissue at or adjacent the GE junction, which includes tissue immediately above and below the sphincter, may bridge over one or both struts 20a, 20b of connector portion 18 at the GE junction as seen in FIG. 2 after bariatric device 10 has been deployed for several weeks or months. Such tissue bridging over struts 20a, 20b may be difficult to remove, such as by merely placing a radial inward force on the struts. It will be appreciated that struts 20a, 20b could not be readily axially displaced with esophageal portion 14 close to the GE junction and cardiac portion 16 against the stomach wall because esophageal portion 14 and cardiac portion 16 are much larger than either strut 20a, 20b and, therefore, could not be pulled through the opening in the bridging tissue. In order to remove struts 20a, 20b to explant device 10, struts 20a, 20b of connector portion 16 of wall 12 are axially displaced, or pulled, from the gastroesophageal junction to remove the connector from the bridging tissue to remove the bariatric device.

Figure 7:
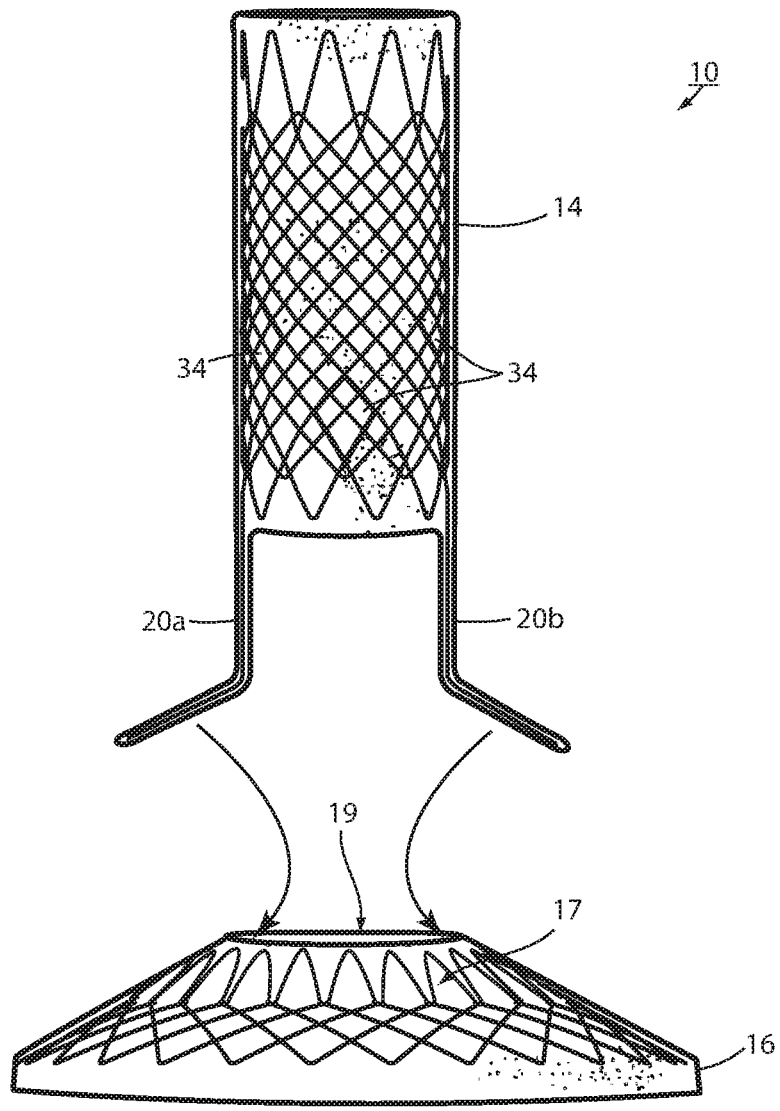
FIG. 7 is a side elevation of a bariatric device showing the principle of removable attachment between the connector portion and the cardiac portion.
Figure 7A:
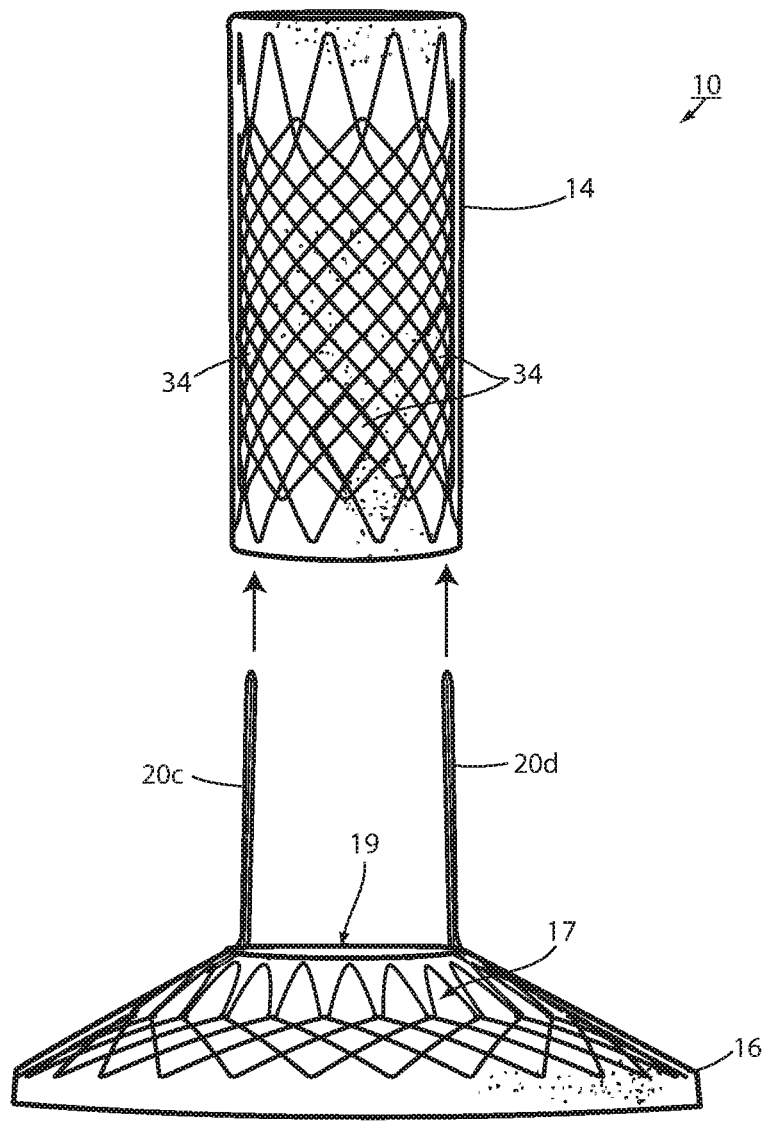
FIG. 7A is the same view as FIG. 7 illustrating an alternative embodiment thereof.

This could at least theoretically be achieved by physically severing the struts, such as using an argon beam coagulator, or the like. In the illustrated embodiments, such axial displacement of the struts is achieved by making struts 20a and 20b separable from the portion of the device wall 12 defining cardiac portion 16 and by separating the struts from the device wall as seen in FIG. 7 or by making struts 20c and 20d separable from the portion of the device wall defining esophageal portion 14 and separating the struts from the device wall as seen in FIG. 7A. Struts 20a, 20b, 20c, 20d are adapted to be separated by being removeably attached with a removable attachment 42 to wall 12. The struts can be separated by removing the removable attachment.

Once free of the cardiac portion 16, struts 20a, 20b may be axial withdrawn, or pulled, proximally through the bridging tissue of the GE junction by axial proximal displacement of esophageal portion 14 in the manner discussed above. Once the struts are withdrawn, the esophageal portion 14 can be retracted proximal, using a removal suture (not shown), or the like. The cardiac portion 16 can be removed from the stomach by drawing it into an overtube inserted in the esophagus or other such method. Once free of esophageal portion 14, struts 20c, 20d may be withdrawn, or pulled, proximally through the bridging tissue of the GE junction by axially distal displacement of cardiac portion 16 into the stomach where it can be removed as discussed above. The esophageal portion 14 can be withdrawn proximally. While the embodiment disclosed in FIG. 7A requires that a force be applied to the cardiac portion 16 to axially separate the struts 20c, 20d from the bridging tissue, an advantage of this embodiment is that the removeable attachment 42 is located at the esophageal portion 14 where it is more easily accessed in order to remove the attachment.

Struts 20a, 20b, 20c, 20d may be each formed from a single continuous metallic filament 38, such as Nitinol or stainless steel that is twisted from distally to proximally as shown in FIG. 4. As filament 38 is wound, several openings 40 may be formed in struts 20a, 20b, 20c, 20d as will be described below. Ends of filament 38 may be woven with the mesh 32 of esophageal portion 14 or of the mesh of the cardiac portion 16 or otherwise attached as seen in FIG. 5. Struts 20a, 20b, 20c, 20d are coated with silicone or other biocompatible material to ease axial withdrawal from the tissue bridging the struts. Also, struts 20a, 20b, 20c, 20d may have an optional elastic portion (not shown) to enhance proximal force placed on cardiac portion 16 to ensure satiety. Also, struts 20a, 20b, 20c, 20d may include a therapeutic agent eluting coating that applies a therapeutic agent, such as an anesthesia, or the like. This coating may elute the agent for a limited period, such as two weeks, after deployment, to ensure pain-free embedding of the struts in the recipient. Alternatively, an agent-dispensing reservoir could be at a distal portion of esophageal portion 14 to dispense a controlled amount of a therapeutic agent, such as an anesthesia to the tissue engaging the struts. In addition to the struts, a therapeutic agent eluting coating may be applied to the area surrounding tissue ingrowth zones 34 and perhaps other areas of device 10. For example, a different type of agent, such as to encourage tissue fibrosis and ingrowth, may be eluted to encourage earlier and stronger long-term fixation.

Figure 8:
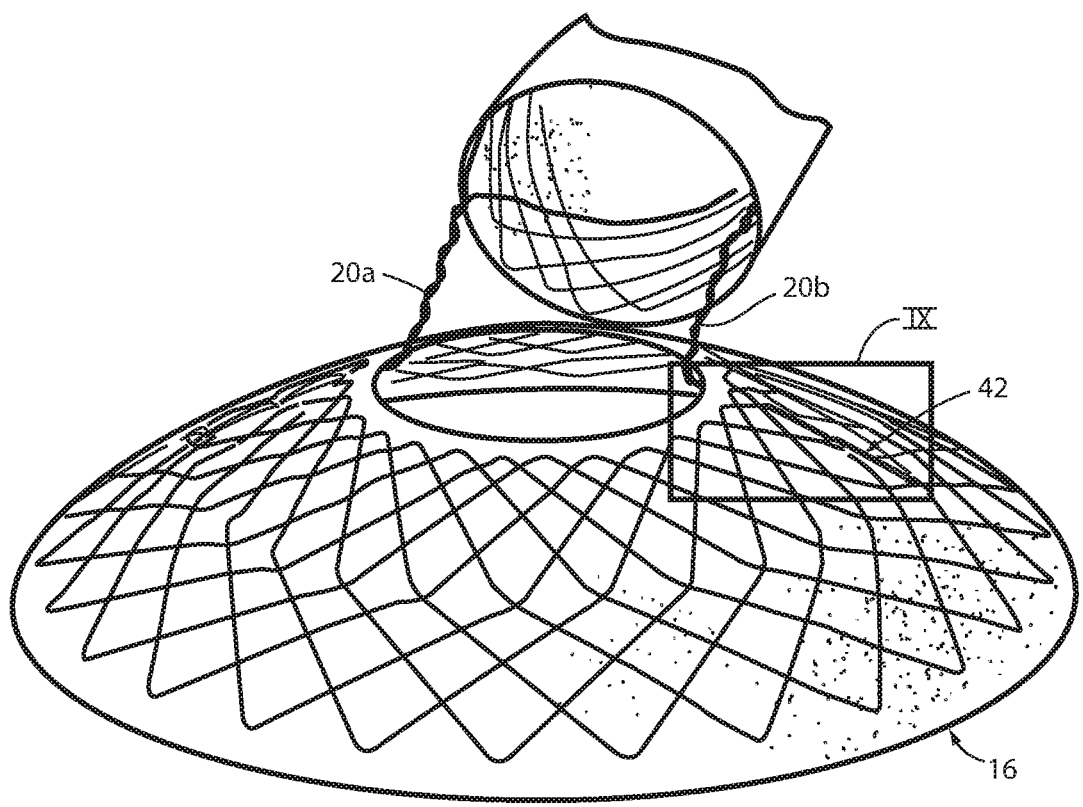
FIG. 8 is a perspective view of the device in FIG. 7 taken from the side and proximal, or top direction illustrating details of the removable attachment.
Figure 9:
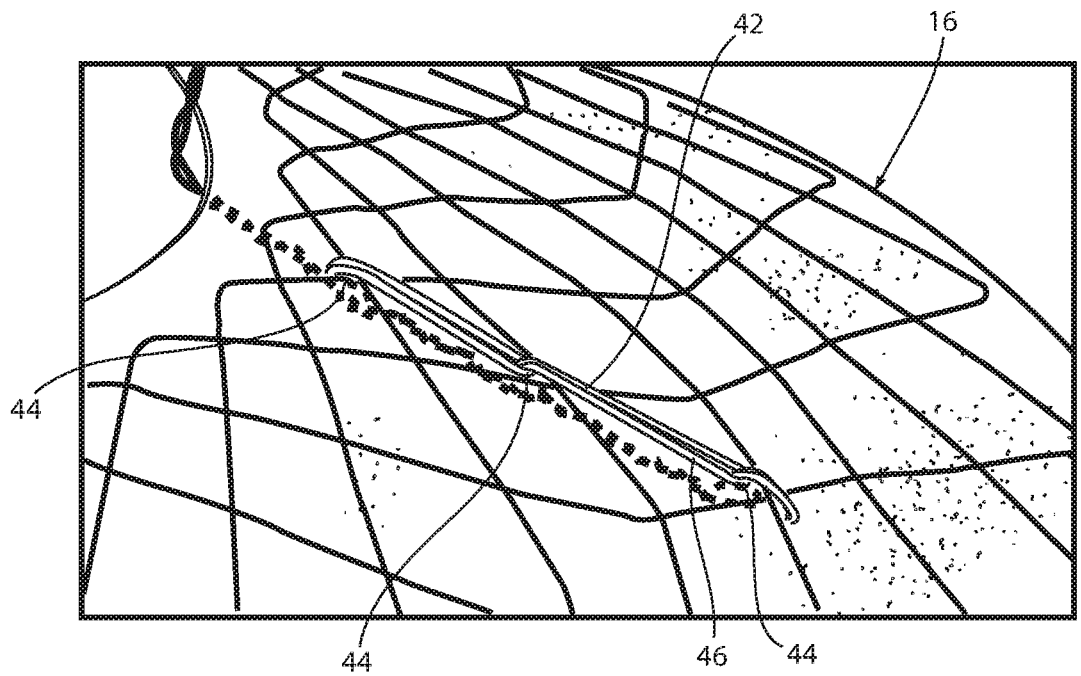
FIG. 9 is an enlarged perspective view of the portion shown at IX in FIG. 8.

In one embodiment, removable attachment 42 includes a separable portion of struts 20a, 20b, 20c, 20d extending along the surface of wall 12 as seen in FIGS. 8 and 9. Openings 40 are arranged to register with intersections 44 in the portion of mesh 32 of wall 12. Removable attachment 42 is illustrated as a chain stitch 46 between one or more openings 40 and corresponding intersections 44. The stich is made with a filament, such as high-strength suture material, or the like. The advantage of a chain stitch, which is known in the art, is that it can be completely removed by severing its filament, such as with an endoscopic scissors or heating device, at any place such along the filament. Once removable attachment 42 is severed at separable portions of both struts 20a, 20b, esophageal portion 14 can be proximally withdrawn thus axially liberating the struts from the captured tissue at the GE junction. Once removeable attachment 42 is severed at separable portions of both struts 20c, 20d cardiac portion 16 can be distally withdrawn thus axially liberating the struts from the captured tissue at the GE junction.

As discussed above, cardiac portion 16 will be in the stomach and can be removed transorally. In addition to a separate chain stich 46 for each strut as shown, it is possible to extend the chain stitch to encompass separable portions of both struts (not shown) so that the chain stitch filament need be severed only once to break both struts free of the wall portion. Also, it is possible that tissue bridging may only occur at one of strut pairs 20a, 20b, such as strut 20b or one of strut pairs 20c, 20d positioned against the GE sphincter at the angle of HIS. As such, removable attachment 42 may be provided for only one strut.

Figure 10:
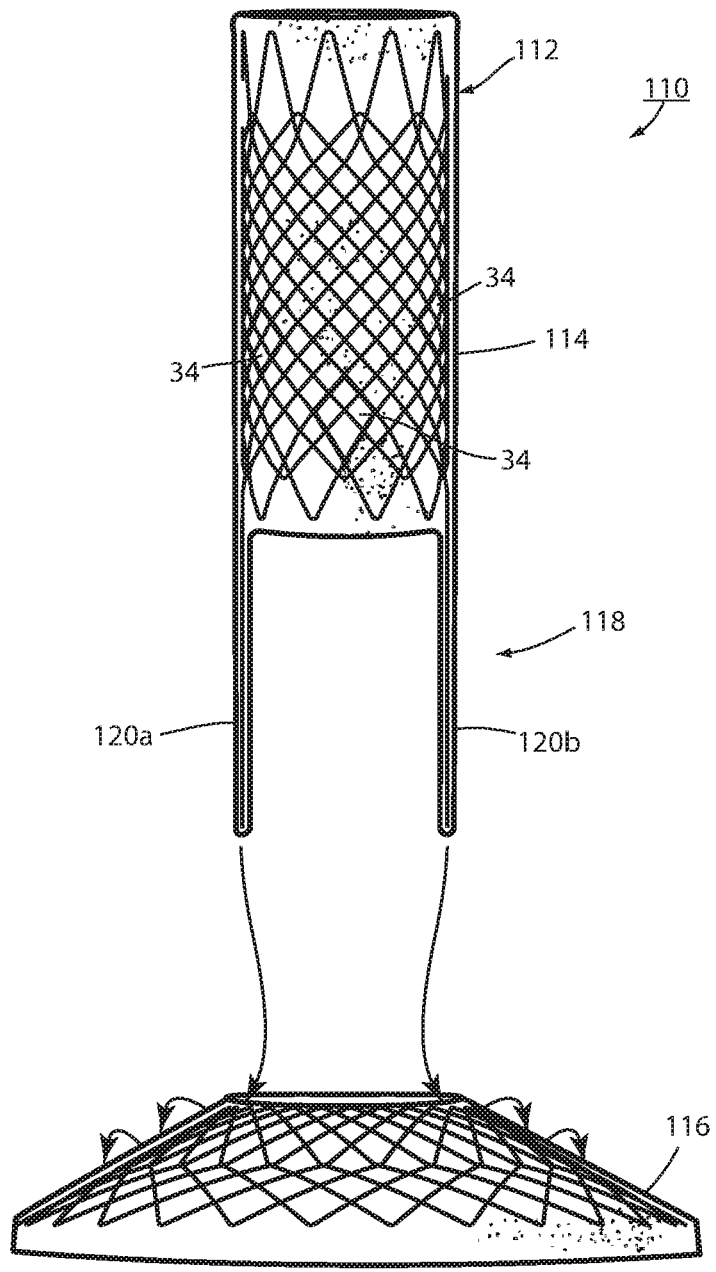
FIG. 10 is the same view as FIG. 7 of an alternative embodiment thereof.
Figure 10A:
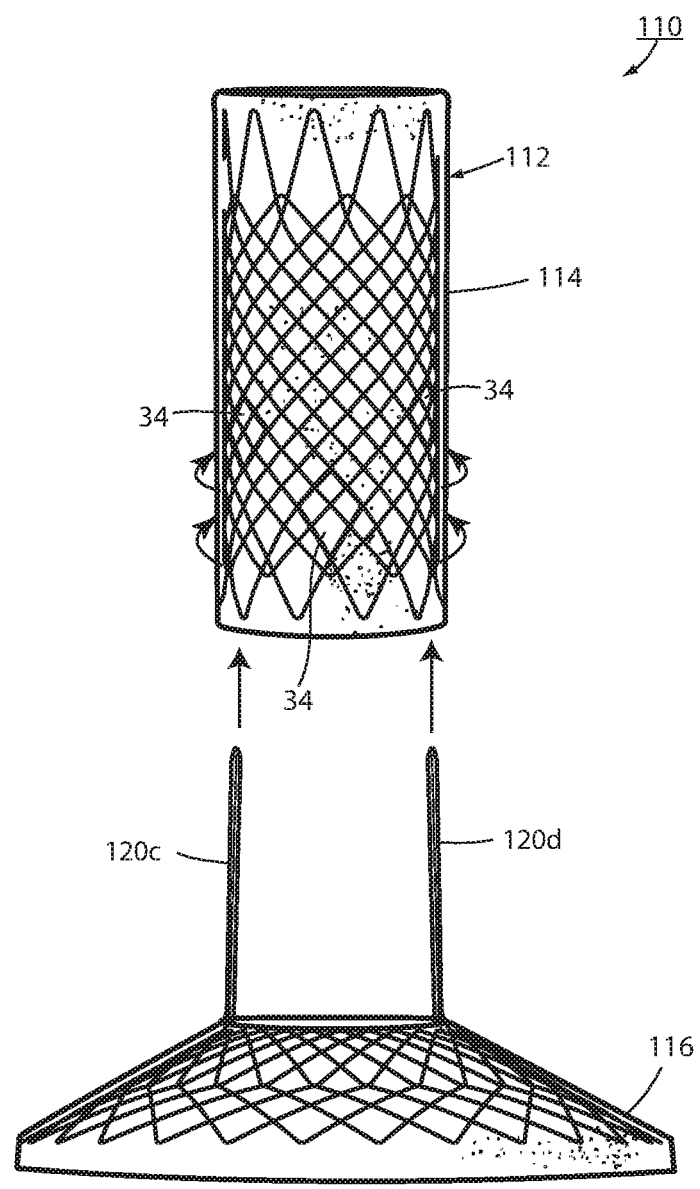
FIG. 10A is the same view as FIG. 10 of an alternative embodiment thereof.

In an alternative embodiment, an intraluminal device 110 includes a wall 112 defining an esophageal portion 114 configured to the size and shape of a portion of the esophagus, a cardiac portion 116 configured to the size and shape of a portion of the cardiac portion of the stomach and a connector 118 (FIGS. 10-13) of which at least a portion passes through the GE junction. Tissue ingrowth openings 134 provide long-term fixation. Intraluminal device 110 is essentially the same as device 10 except that connector portion 118 is removeably connected with wall 112 by an alternative removable attachment 142. In FIG. 10, separable portions of struts 120a, 120b making up connector portion 118 extend over some of intersections 144 of the mesh 132 of cardiac portion 116 and under other ones of the intersections 144 at cardiac portion 116 as seen in FIGS. 10-13. In FIG. 10A, separable portions of struts 120c, 120d extend over some intersections of the mesh of esophageal portion 114 and under other ones of the intersections at the esophageal portion 114 of wall 112.

Figure 11:
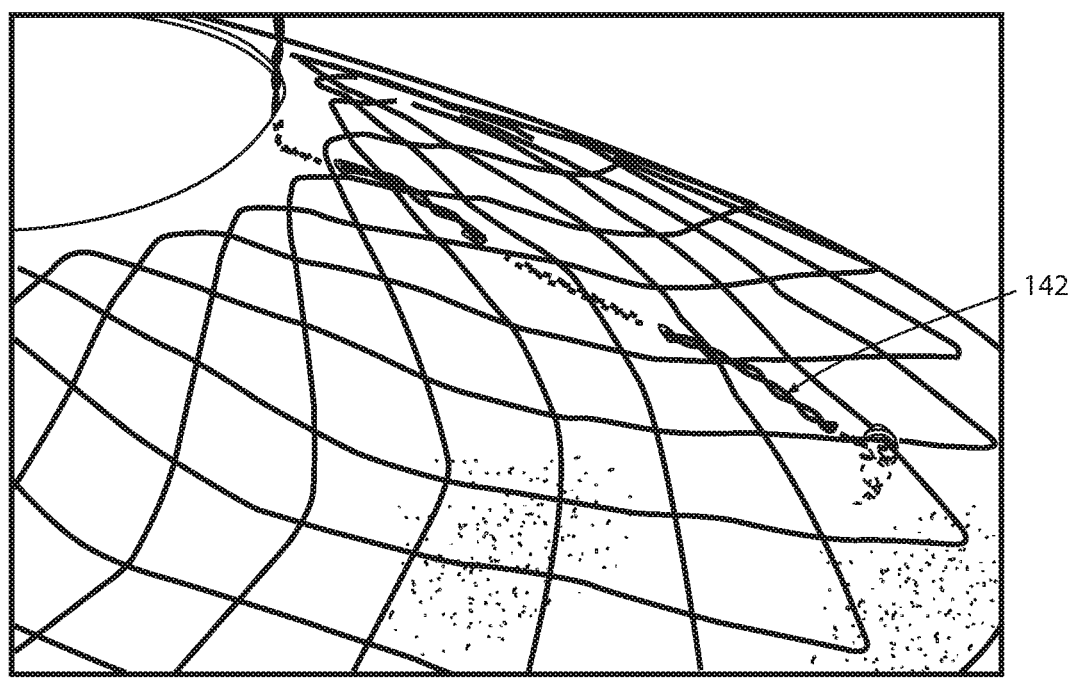
FIG. 11 is a perspective view taken from the side and proximal or top showing a removable attachment between the connector portion and the cardiac portion of the embodiment in FIG. 10.
Figure 12:
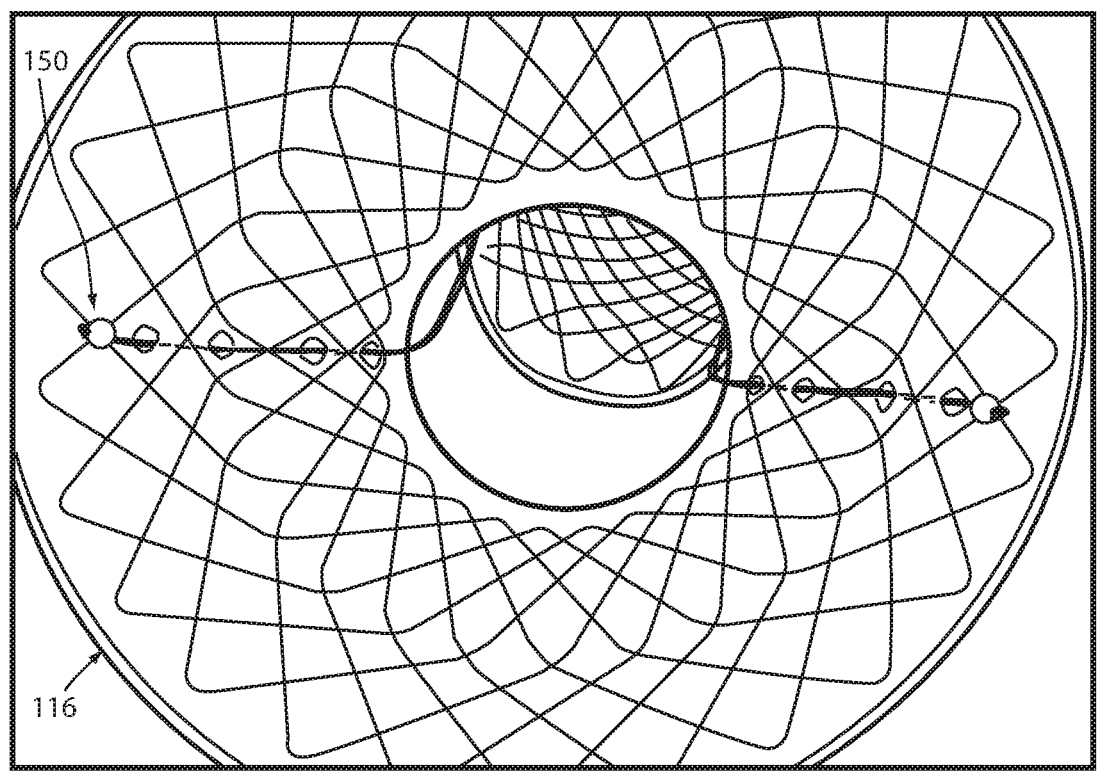
FIG. 12 is a bottom or distal plan view of the removable attachment in FIG. 11.
Figure 13:
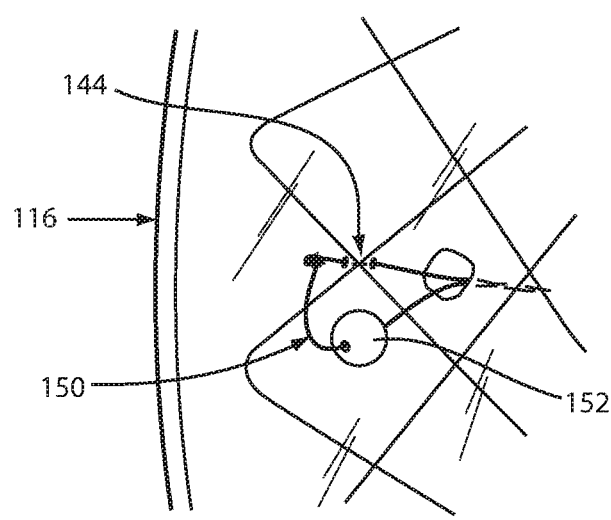
FIG. 13 is an enlarged view of the severable knot in FIG. 12.

Removeable attachment 142 includes a severable knotted filament 150 at a distal end of each strut secures an end of the separable portion of the strut to the wall as seen in FIGS. 11-13. In this manner, severing of filament 150 allows each strut to pull away from the wall portion. The severable filament 150 may include an extender, such as a bead 152, to enhance access to the filament to assist in severing the filament. Bead 152 is strung on filament 150. Filament 150 may extend between both separable ends of the struts so that the filament needs to be severed at one place to free both struts from the wall portion.

Figure 14:
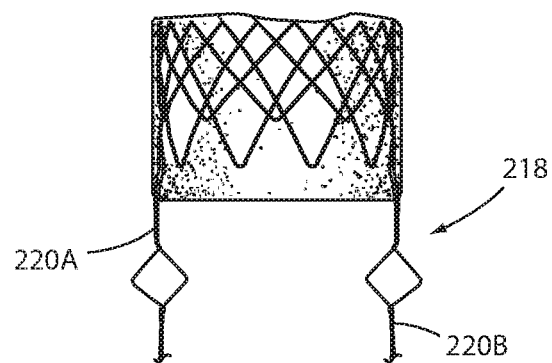
FIG. 14 is a side elevation of an alternative embodiment of a connector portion.

It should be understood that the tissue bridging over struts 20a, 20b, 20c, 20d, 120a, 120b, 120c, 120d which are elongated filaments that provide a wall characteristic that fixes the wall of the respective struts to the GE region through growth of tissue, can be useful as all or part of long-term fixation of device 10, 110. Such long-term fixation may be enhanced by adding length to similar struts 220a, 220b shown in FIG. 14. This may be accomplished by providing a knee to the strut, such as branching to the filaments as seen in FIG. 14. This may be accomplished by leaving the filaments non-twisted so that each filament forms a separate bridge that bows outwardly. Once the attachment to the wall portion (not shown in FIG. 14) is severed, the multiple filament branches to the strut can be individually pulled through the same opening in the mucosa caused by the bridging. Struts 20a, 20b, 20c, 20d 220a, 220b, 220c, 220d can have an outward knee to further engage the mucosa to promote tissue bridging.

Figure 15:
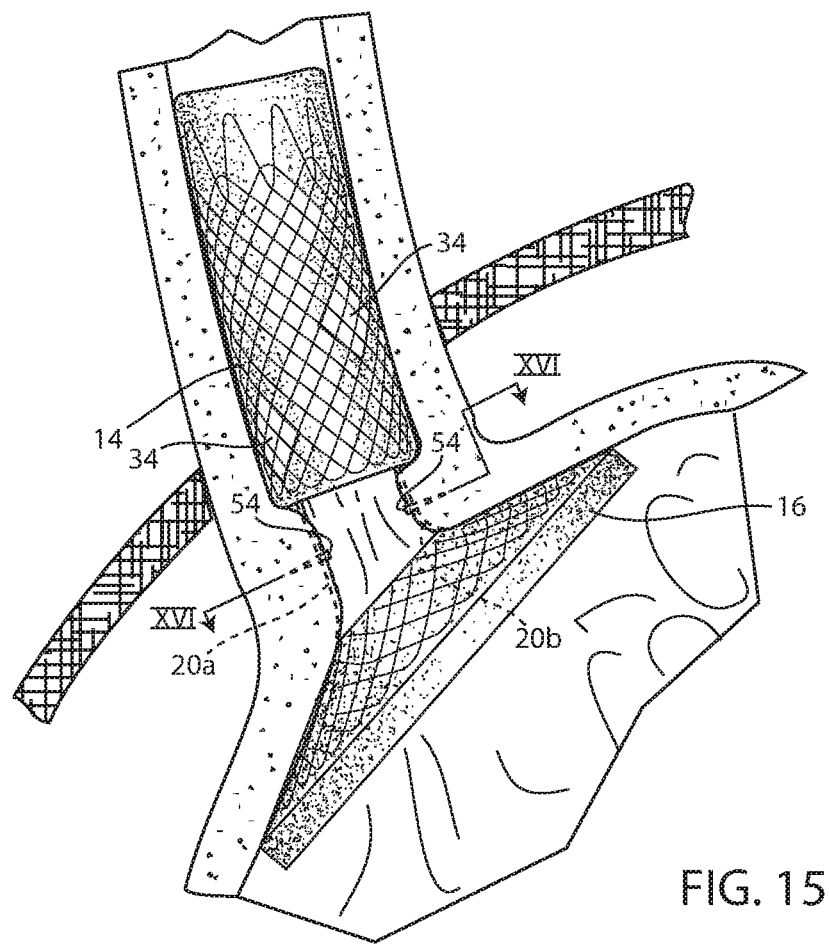
FIG. 15 is a side elevation of an alternative embodiment showing enhancement of mucosal bridging.
Figure 16:
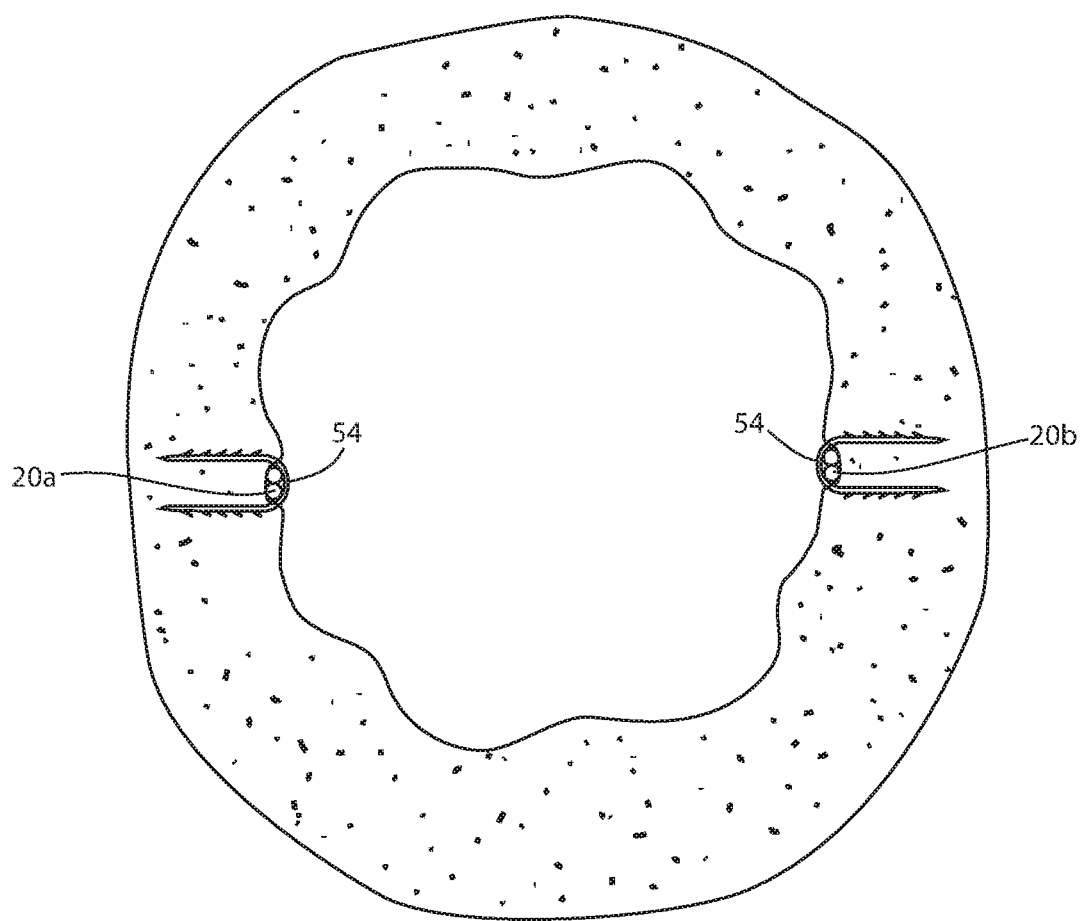
FIG. 16 is a sectional view taken along the lines XVI-XVI in FIG. 15.
Figure 17:
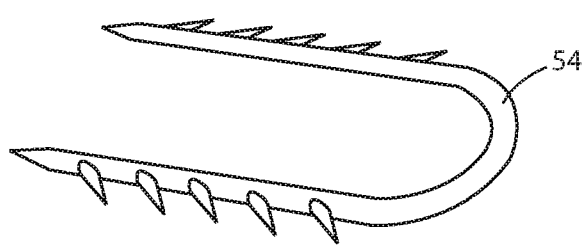
FIG. 17 is a perspective view of a clip.
Figure 18:
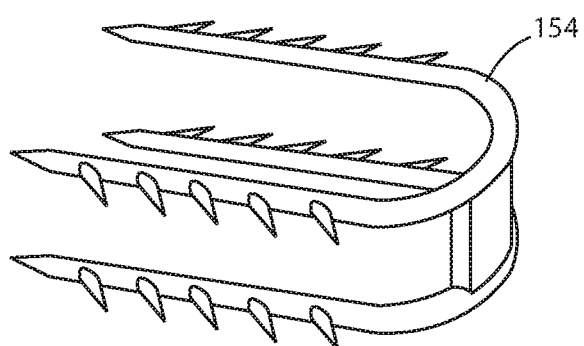
FIG. 18 is the same view as FIG. 17 of an alternative embodiment thereof.

Also, short-term and/or long-term fixation using the struts can be enhanced by applying tissue penetrative fasteners in the form of retainers 54 to the bridging mucosa (FIGS. 15-17). Retainers 54 include a U-shaped body having a pointed end with barbs 55. This allows the retainer to be inserted through the mucosa onto the musculara and the barbs to hold the retainer in place. Retainers 54 can be bioabsorbable so that they fall away after the passage of time when mucosal bridging is secure. Alternatively, retainers 154 include coupled U-shaped portions, each with barbs 155 in order to enhance attachment to the musculara as seen in FIG. 18. Application of suction to the esophagus of the recipient will tend to cause the tissue of the EG junction to come together around the respective strut to assist in placement of retainers 154 to bring the tissue portions together around the strut to facilitate tissue capture of the strut using the principles disclosed in commonly assigned U.S. Pat. No. 8,894,670, the disclosure of which is hereby incorporated herein by reference in its entirety.

Other forms of tissue penetrating fasteners can be used, such as EZ clip or a quick-clip, both available from Olympus. In addition to promotion of tissue bridging over the strut(s) 20a, 20b, 20c, 20d, 120a, 120b, 120c, 120d, the retainers 54, 154 may provide resistance to distal migration of esophageal member 14. This helps to provide tension on the struts, thus ensuring cardiac member 16, 116 is in contact with the cardiac portion of the stomach. Thus, clip 54, 154 may provide both immediate short-term fixation of the bariatric device and promote long-term fixation via fusion of tissue bridging struts 20a, 20b, 20c, 20d, 120a, 120b, 120c, 120d.

An intraluminal device 210 is shown in FIGS. 19-23 in which another technique is shown for fixation of the intraluminal device against peristalsis in the lumen. Device 210 includes a wall 212 defining an esophageal portion 214 having a size and shape corresponding to a portion of the esophagus at the GE region, a cardiac portion 216 having a size and shape corresponding to a portion of the cardia or a cardiac portion of the stomach, and a connector 218 connecting the esophageal portion to the cardiac portion. At least a portion of connector 218 passes through the GE junction. Connector 218 is made up of two elongated struts 220a, 220b, both of which pass through the GE junction. The struts elongated shape provides a wall characteristic that provides, at least in part, long-term fixation of wall 212 to the GE region though growth of tissue around each strut. Struts 220a, 220b include a biocompatible coating, such as silicone, or the like, that allows the struts to be axially separated from the GE junction once severing of the removable connector (not shown in FIG. 19) separates the strut from the wall portion 212 in the manner previously described.

An alternative issue penetrating fastener 256 around each strut 220a, 220b includes a series of tissue penetrating barbs 257 that are capable of penetrating mucosa, submucosa, and/or musculara at the GE junction when pressed against the tissue. Penetrating barb 257 may have fishhook, or arrowhead, features to avoid withdrawal of the barbs once inserted. Fastener 256 may be formed around the strut as part of manufacture or may be a separate device as shown in FIG. 20 having a slit that allows it to be positioned around the strut at deployment.

In addition to the dimensions of each strut providing a wall characteristic that causes tissue to grow around the strut, each fastener 256 may have a wall characteristic 259 facing away from the tissue of the GE junction that enhances long-term fixation of wall 212 to the GE region through promoting growth of tissue around the respective strut. Wall characteristic 259 may be a roughened or fenestrated surface, a surface impregnated with a tissue growth agent, or the like. Wall characteristic 259 may include bars similar to barbs 257 such that application of suction to the esophagus of the recipient tends to draw the tissue of the GE junction around the wall characteristic 259 where it is ensnared by the barbs of wall characteristic 259 to further enhance short-term fixation. Fastener 256 may be made in whole or in part from a bioabsorbable material to resorb after tissue grows around the strut to provide long-term fixation of device 210. The resorption of the fastener 256 avoids fastener 256 from impeding axial withdrawal of the struts for device explantation.

Another tissue penetrating fastener 258 having tissue penetrating barbs 257 may be at a portion of esophageal member 214, such as at its distal rim, in order to provide additional temporary fixing of device 210 at the GE region. Fastener 258 is shown formed or otherwise attached to a distal rim of esophageal portion 214 but could be located at any portion of esophageal portion 214. Fastener 258 only provides temporary fixing of device 210 and therefore does not include a wall characteristic 259 that enhances long-term fixing of wall 212 to the GE region. Fastener 258 is made in whole or in part from bioabsorbable material in order to resorb after long-term fixation is in place to avoid interference with explantation of device 240.

Figure 23:
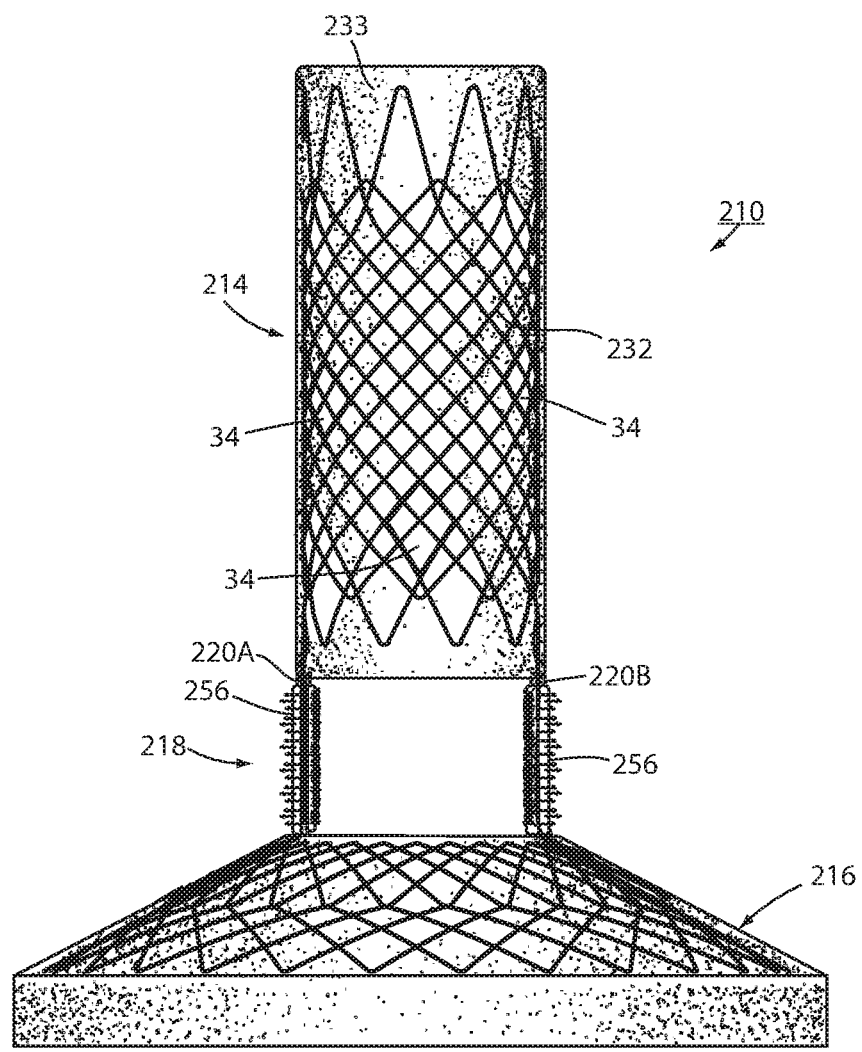
FIG. 23 is the same view of the same device of FIG. 19 of an alternative embodiment.

As seen in FIG. 23, device 210 may include a fastener 256 at one or both struts 220a, 220b making up connector 218, but not include a fastener 258 at the esophageal portion 214. Of course device 210 may include a tissue penetrating fastener 258 without a combination temporary and permanent fixing device 256 since the elongated slender nature of struts 220a, 220b are a wall characteristic that fixes wall 212 to the GE region through growth of tissue to provide long-term fixation.

Figure 24:
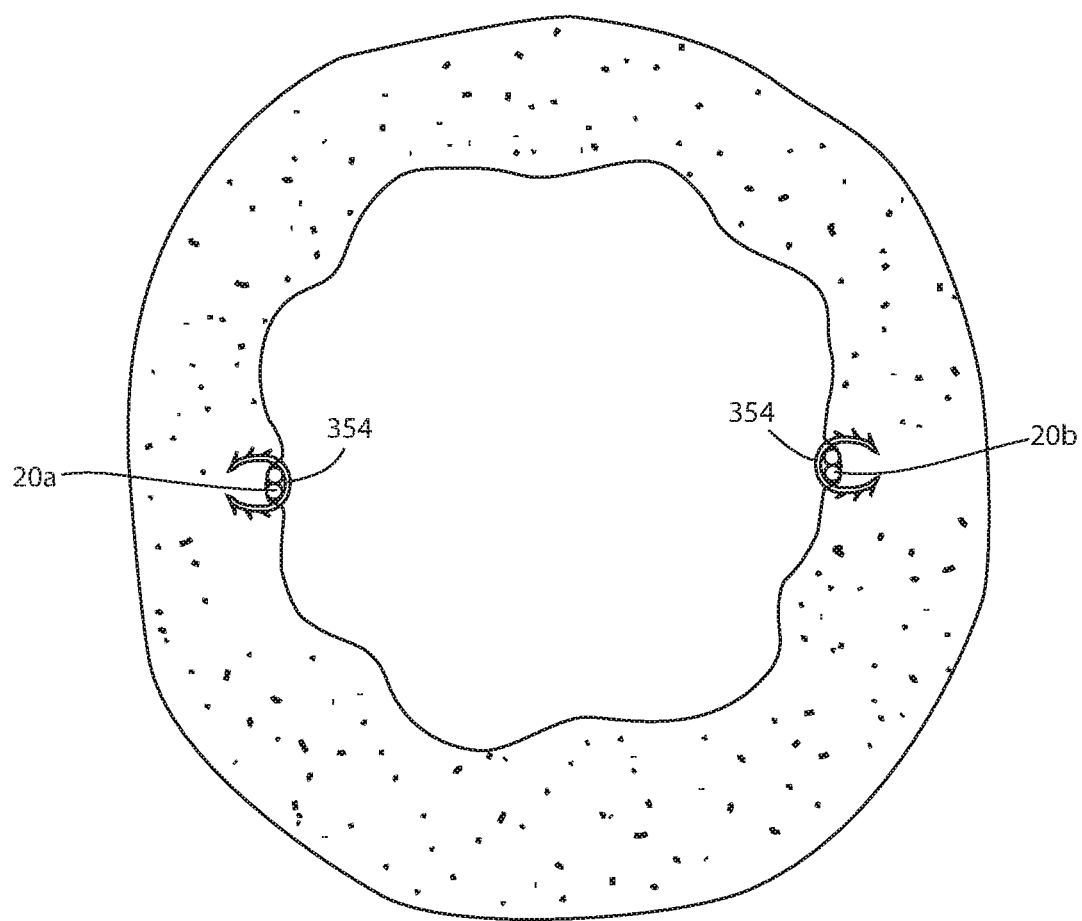
FIG. 24 is the same view as FIG. 16 of an alternative embodiment.

An alternative retainer 354 shown in FIG. 24 is a clip that closes around the strut 20a, 20b, 20c, 20d, 2120a, 120b, 120c, 120d, or which only struts 20a and 20b are shown, after the device 10 is positioned at the GE region. Clip 354 may be spring-loaded or made from memory material to close around the strut upon being positioned in the tissue or may be mechanically deformed by a mechanism that is endoscopically deployed. Suction applied to the esophagus of the recipient may be applied to assist in drawing tissue around the struts to facilitate a clip being inserted into the tissue.

FIG. 26 illustrates another tissue penetrating fastener 258b that may be used in whole or in part for short-term fixation of device 210 against distal migration. Fastener 258b may be placed at a proximal end portion of esophageal portion 214. Fastener 258b has barbs 257b that at least partially penetrate the tissue of the esophagus to provide short-term fixation. Fastener 258b may be made in whole or in part from a resorbable material in order to be absorbed in the recipient after long-term fixation has occurred. Barbs 257b are illustrated as being distally angled so that device 210 can be adjusted proximally during deployment without impediment from the bars which are still capable of resisting distal migration.

Figure 27:
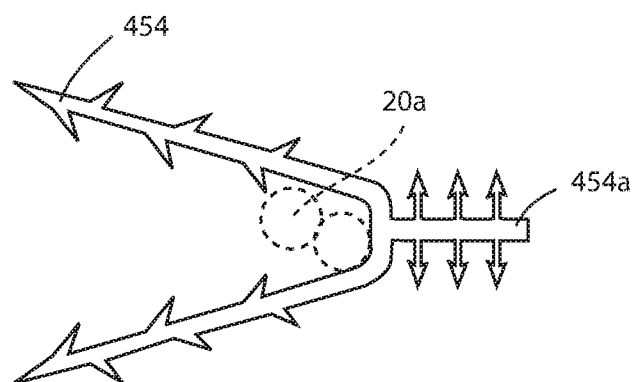
FIG. 27 is a plan view of an alternative embodiment of a clip.
Figure 28:
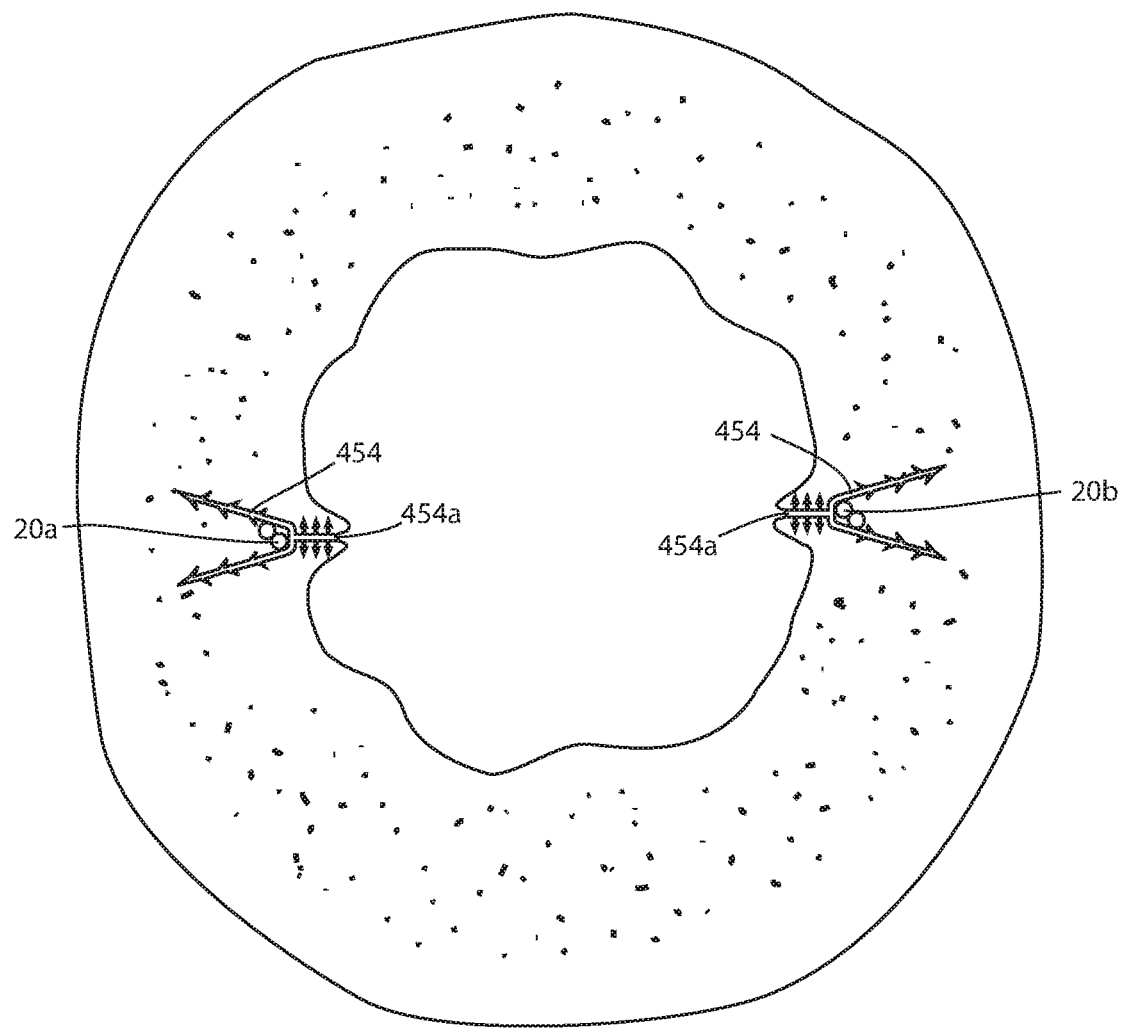
FIG. 28 is the same view as FIG. 24 showing the clip in FIG. 27 applied.

FIGS. 27 and 28 illustrate yet another alternative tissue penetrating retainer 454 that can be used for short-term fixation of the intraluminal device 10, 110, 210. Retainer 454 is positioned along a strut up against the esophageal portion. Retainer 454 is barbed to be retained. In the tissue of the GE junction as shown in FIG. 28 includes a tissue attachment portion 454a. After retainer 454 is over the strut and inserted into the tissue (either as part of positioning the device or after the device is positioned), suction may be applied to the esophagus which will tend to draw tissue around the strut where it will be retained by barbs or other surface of tissue attachment portion 454a.

Figure 25:
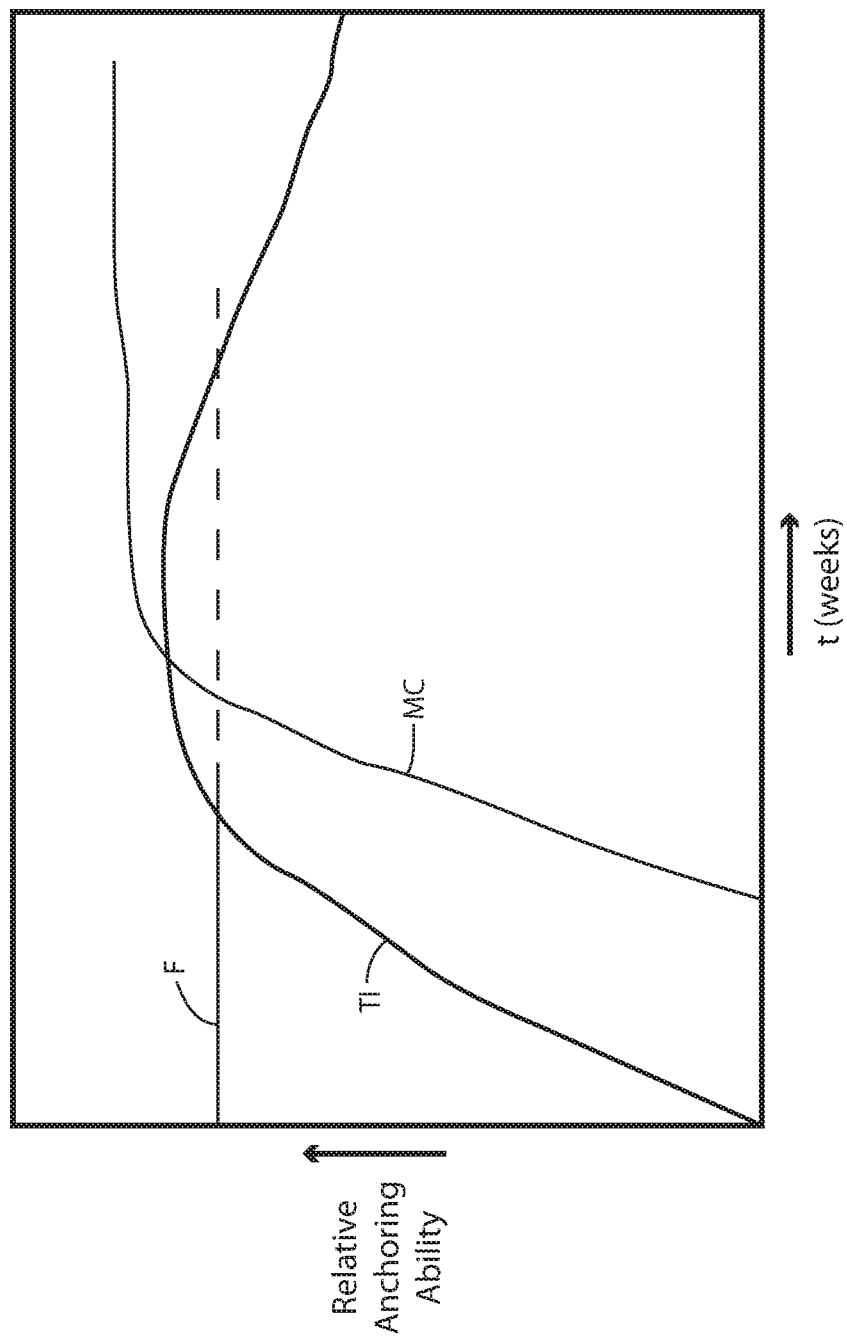
FIG. 25 is a chart illustrating relative anchoring strength of different anchoring techniques over time.

Thus, it is seen that aspects of the present invention encompass short-term and long-term fixation of an intraluminal device, such as a bariatric device, in a lumen, such as the gastro-esophageal region of the recipient. The long-term fixation uses the body's response to the presence of the device to provide long-term fixation. Short-term fixation, such as one or more tissue penetrating fasteners, provide fixation of the device while long-term fixation develops. Once long-term fixation develops, the short-term fixation may slough off or be absorbed as it is no longer needed. Even multiple different types of long-term fixation may be provided in order to provide optimal fixation at different times after deployment. For an example, FIG. 25 illustrates relative fixation, shown on the Y-axis for different time intervals after deployment, shown on the Y-axis. When the device is deployed, at the origin of the graph, temporary fixation F maintains the intraluminal device in place. After deployment, the tissue ingrown TI begins to develop and increases over time. Sometime after deployment, temporary fixation F may be eliminated, such as by absorption of resorbable sutures or filament loops, as depicted by the dashed horizontal line. By that time, the tissue ingrowth TI should be sufficiently strong to provide long-term fixation. An additional form of long-term fixation may be provided by mucosal capture MC around the struts of the bariatric device. While the mucosal capture MC may take longer to develop than the tissue ingrowth TI, it may provide long-term fixation even if the tissue ingrowth fixation TI weakens over time.

It should be understood that FIG. 25 is intended to illustrate conceptual relationships and is not based upon physical measurements. It should also be understood that the timeline in FIG. 25 may be measured over days, weeks or months. However, it is expected that tissue ingrowth TI or mucosal capture MC should be sufficient to provide fixation by itself within about four (4) days to one or more weeks.

It may also be possible to eliminate tissue ingrown TI and rely exclusively on mucosal capture MC in order to provide long-term fixation. Such alternative may include using one of the illustrated retainers around one or both struts in order to provide short-term fixation while long-term fixation develops, such as by mucosal capture MC around each of the struts. By providing both short-term and long-term fixation at the struts, the intraluminal device should be simpler to deploy and explant. Deployment may occur by the insertion of a retainer clip at one or both struts or even by a self-deploying retainer that penetrates tissue at the GE junction upon positioning of the device in the lumen of the recipient. With long-term fixation provided at the struts alone, the device can be explanted by separating the separable struts and axially retracting the struts from the GE junction by proximally withdrawing the esophageal member from the esophagus. The cardiac member can then easily be retrieved from the stomach. Because tissue ingrowth is not employed in such embodiment, there is no need to remove tissue from the tissue ingrown zones.

The intraluminal device 10, 110, 210 may be made adjustable in order to adjust or titrate the amount of stress on the cardiac portion of the stomach, such as by using a bladder or bladders on the proximal surface of the cardiac portion using the principles disclosed in International Application Publication No. WO2015/031077, the disclosure of which is hereby incorporated herein by reference in its entirety. Besides providing for adjustability, such bladder(s) may be filed with a fluid made of a lighter-than-air gas, such as helium, hydrogen, or the like, in order to assist in urging the cardiac member against the cardiac portion of the stomach in order to at least partially provide short- or long-term fixation.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. A method of fixation of an intraluminal device to resist distal migration in a mammalian lumen or hollow organ that is subject to peristalsis, the intraluminal device comprising spaced apart wall portions connected with a connector, wherein said wall portions are configured to the size and shape of a portion of the lumen or hollow organ and said connector is configured to be positioned against a wall of the lumen or hollow organ, said method comprising:
    positioning the intraluminal device in a mammalian lumen or hollow organ that is subject to peristalsis;
    fixing said device in the lumen or hollow organ against distal migration with the connector positioned against the lumen, wherein tissue lining the lumen or hollow organ grows around said connector with the passage of time; and
    explanting the device after tissue grows around the connector including separating the connector from at least one of said wall portions and withdrawing the connector from the tissue around the connector.

2. The method as claimed in claim 1 wherein said wall portions are joined with said connector prior to said positioning.

3. The method as claimed in claim 1 wherein said connector comprises at least one filament that is coated with a bio-compatible material, wherein said bio-compatible material extends around said at least one filament from one of said wall portions to the other of said wall portions.

4. The method as claimed in claim 1 including a removable attachment connecting said connector with said at least one of said wall portions and wherein said separating comprises removing said removable attachment.

5. The method as claimed in claim 4 wherein said removable attachment comprises a severable filament.

6. The method as claimed in claim 1 including a fixation system that is configured to resist distal migration of said wall in the lumen wherein said fixation system includes said connector having a configuration to facilitate tissue of the lumen growing around said connector.

7. The method as claimed in claim 6 wherein said fixation system includes a tissue penetrating fastener configured to engage the connector with tissue of the lumen.

8. The method as claimed in claim 1 wherein said intraluminal device comprises an esophageal stent, an anti-reflux device, a nasal gastric tube, an intestinal sleeve, a bariatric device or a metabolic disease treatment device.

9. A method of fixation of an intraluminal device at the gastroesophageal (GE) region of the recipient to resist distal migration, the device having a wall defining an esophageal portion that is configured to the size and shape of a portion of the esophagus, a cardiac portion that is configured to the size and shape of the cardiac portion of the stomach and a connector connecting said esophageal and cardiac portions, said method comprising:
    positioning said device at the GE region with the esophageal portion in the esophagus, the cardiac portion at the cardiac portion of the stomach and at least a portion of said connector at the gastroesophageal (GE) junction, wherein tissue at the GE junction grows around at least a portion of the connector with the passage of time; and
    explanting the device after tissue has grown around the portion of the connector including separating the connector from at least one selected from said esophageal portion and said cardiac portion, withdrawing the connector from the tissue grown around the portion of the connector at the gastroesophageal junction.

10. The method as claimed in claim 9 wherein said connector is separably connected with said cardiac portion.

11. The method as claimed in claim 9 wherein said connector is separably connected with said esophageal portion.

12. The method as claimed in claim 9 wherein a separable portion of said connector is separably connected with said wall with a removable attachment.

13. The method as claimed in claim 12 wherein the separable portion of said connector extends along said wall and wherein said removable attachment comprises a severable filament between said separable portion and said wall.

14. The method as claimed in claim 9 wherein said connector comprises a filament and a biocompatible coating over said filament.

15. The method as claimed in claim 9 wherein said connector includes a therapeutic agent eluting coating.

16. The method as claimed in claim 9 including a therapeutic agent dispensing reservoir at a distal portion of said esophageal portion and dispensing a therapeutic agent.

17. The method as claimed in claim 9 wherein said intraluminal device comprises a bariatric device used to treat excess body mass or a metabolic device used to treat metabolic disease.

18. A method of fixation of an intraluminal device at the gastroesophageal (GE) region of a recipient to resist distal migration, the device having a wall defining a cardiac portion that is configured to the size and shape of the cardiac portion of the stomach, an esophageal portion that is configured to the size and shape of a portion of the esophagus and a connector connecting said esophageal portion and said cardiac portion, said method comprising:
    positioning the device at the GE region with at least a portion of the connector passing through the GE junction wherein tissue will grow to the wall to provide long-term fixation of the wall to the GE region of the recipient to resist distal migration;
    temporarily fixing the device at the GE region to resist distal migration while tissue grows to the wall; and
    wherein the temporarily fixing and the long-term fixation both at least partially occur at the portion of the connector at the GE junction.

19. The method as claimed in claim 18 wherein said connector being an elongated filament.

20. The method as claimed in claim 18 including a tissue ingrowth promotion surface configuration of said connector.

21. The method as claimed in claim 20 wherein said tissue ingrowth promotion surface configuration faces inwardly away from the GE junction.

22. The method as claimed in claim 21 wherein said temporary fixing comprises fixing the device at least partially at the GE Junction with a tissue penetrating fastener.

23. The method as claimed in claim 22 including facing said tissue penetrating fastener outwardly toward the GE junction.

24. The method as claimed in claim 22 including engaging said tissue penetrating fastener at the GE junction as a function of deploying said device at the GE region of the recipient.

25. The method as claimed in claim 22 including applying said tissue penetrating fastener to tissue at said connector after deployment of said device at the GE region of the recipient.

26. The method as claimed in claim 22 including positioning said tissue fastener is positioned in part at said esophageal portion.

27. The method as claimed in claim 26 including positioning said tissue penetrating fastener in part at said esophageal portion to penetrate the tissue of the lumen upon deployment of the device.

28. The method as claimed in claim 21 wherein said tissue penetrating fastener is made at least in part from a bioabsorbable material.

29. The method as claimed in claim 18 wherein said connector comprises a filament and a biocompatible coating over said filament.

30. The method as claimed in claim 18 wherein said connector includes a therapeutic agent eluting coating.

31. The Method as claimed in claim 18 wherein said device comprises a bariatric device used to treat excess body mass or a metabolic device used to treat metabolic disease.

32. A method of fixation of an intraluminal device at the gastroesophageal (GE) region of the recipient to resist distal migration, the device having a wall defining an esophageal portion that is configured to the size and shape of a portion of the esophagus, a cardiac portion that is configured to the size and shape of the cardiac portion of the stomach and a connector connecting said esophageal and cardiac portions, said method comprising:
    positioning said device at the GE region with the esophageal portion in the esophagus, the cardiac portion at the cardiac portion of the stomach and at least a portion of said connector at the gastroesophageal (GE) junction, wherein tissue at the GE junction encompasses at least a portion of the connector;
    explanting the device after tissue has encompassed the portion of the connector including separating the connector from at least one selected from said esophageal portion and said cardiac portion in order to separate the intraluminal device from the tissue encompassing the portion of the connector at the gastroesophageal junction;
    wherein a separable portion of said connector is separably connected with said wall with a removable attachment, wherein the separable portion of said connector extends along said wall and wherein said removable attachment comprises a severable filament between said separable portion and said wall; and
    wherein said wall comprises a structural mesh defining intersections and covered with a biocompatible coating and wherein said separable portion of said connector comprises at least one opening defined by said connector that align with at least one intersection of said mesh and wherein said severable filament extends between said at least one opening and said at least one intersection.

33. The method as claimed in claim 32 wherein said at least one opening comprises a plurality of openings and said at least one intersection comprises a plurality of intersections that are aligned with said plurality of openings and said severable filament is formed as a chain stitch between said plurality of openings and said plurality of intersections.

34. A method of fixation of an intraluminal device at the gastroesophageal (GE) region of the recipient to resist distal migration, the device having a wall defining an esophageal portion that is configured to the size and shape of a portion of the esophagus, a cardiac portion that is configured to the size and shape of the cardiac portion of the stomach and a connector connecting said esophageal and cardiac portions, said method comprising:
    positioning said device at the GE region with the esophageal portion in the esophagus, the cardiac portion at the cardiac portion of the stomach and at least a portion of said connector at the gastroesophageal (GE) junction, wherein tissue at the GE junction encompasses at least a portion of the connector;
    explanting the device after tissue has encompassed the portion of the connector including separating the connector from at least one selected from said esophageal portion and said cardiac portion in order to separate the intraluminal device from the tissue encompassing the portion of the connector at the gastroesophageal junction;
    wherein a separable portion of said connector is separably connected with said wall with a removable attachment; and
    wherein said wall comprises a structural mesh defining intersections and covered with a biocompatible coating wherein a separable portion of said connector extending over at least one of said intersections and under at least one other of said intersections and wherein said removable attachment is between said separable portion and said mesh keeping said connector from sliding with respect to said intersections.

35. The method as claimed in claim 34 wherein said removable attachment comprises a filament between said separable portion and said mesh.

36. The method as claimed in claim 35 including a bead on said filament to provide access to said filament.

37. The method as claimed in claim 34 wherein said connector extends over a plurality of intersections and under at least one intersection between said plurality of intersections.

38. A method of fixation of an intraluminal device at the gastroesophageal (GE) region of the recipient to resist distal migration, the device having a wall defining an esophageal portion that is configured to the size and shape of a portion of the esophagus, a cardiac portion that is configured to the size and shape of the cardiac portion of the stomach and a connector connecting said esophageal and cardiac portions, said method comprising:
    positioning said device at the GE region with the esophageal portion in the esophagus, the cardiac portion at the cardiac portion of the stomach and at least a portion of said connector at the gastroesophageal (GE) junction, wherein tissue at the GE junction grows around at least the portion of the connector with the passage of time; and
    wherein said connector is separably connected with at least one chosen from said esophageal portion and said cardiac portion and explanting the intraluminal device after tissue has grown around the portion of the connector including separating in situ the connector from said at least one selected from said esophageal portion and said cardiac portion in order to separate the intraluminal device from the tissue grown around the portion of the connector in order to explant the intraluminal device.

* * * * *

UNITED STATES PATENT AND TRADEMARK OFFICE
CERTIFICATE OF CORRECTION

PATENT NO. : 10,682,219 B2
APPLICATION NO. : 15/534891
DATED : June 16, 2020
INVENTOR(S) : James A. Foote, Frederick J. Walbum and Randal S. Baker It is certified that error appears in the above-identified patent and that said Letters Patent is hereby corrected as shown below:

In the Specification

Column 1
Line 45, "explanation," should be --explantation--
Line 55, "Explanation," should be --Explantation--
Line 57, "explanation," should be --explantation--

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*